United States Patent [19]

Rosenberg

[11] Patent Number: 5,266,688
[45] Date of Patent: * Nov. 30, 1993

[54] POLYNUCLEOTIDE SEQUENCE FOR PRODUCTION OF GLUCOSE OXIDASE IN RECOMBINANT SYSTEMS

[75] Inventor: Steven Rosenberg, Oakland, Calif.

[73] Assignee: Chiron Corporation, Emeryville, Calif.

[*] Notice: The portion of the term of this patent subsequent to Mar. 10, 2009 has been disclaimed.

[21] Appl. No.: 848,406

[22] Filed: Mar. 6, 1992

Related U.S. Application Data

[63] Continuation of Ser. No. 366,377, Jun. 19, 1989, Pat. No. 5,094,951, which is a continuation of Ser. No. 209,530, Jun. 21, 1988, abandoned.

[51] Int. Cl.$^5$ .............................. C12N 15/53
[52] U.S. Cl. ................. 536/23.2; 435/320.1

[58] Field of Search ............... 536/27, 23.2

[56] References Cited

PUBLICATIONS

Pazur et al. Biochemistry, vol. 3, pp. 578–583 (1964).
Suggs et al. PNAS, vol. 78, pp. 6613–6617 (1981).
Lehninger, Albert, Biochemistry, pp. 97–98 (1970).

*Primary Examiner*—Richard A. Schwartz
*Assistant Examiner*—Gary L. Brown
*Attorney, Agent, or Firm*—Barbara G. McClung; Kenneth M. Goldman; Robert P. Blackburn

[57] ABSTRACT

The present invention provides recombinant polynucleotides which encode glucose oxidase (GO). It also provides recombinant expression systems which produce, and when desired, secrete active GO and GO analogs into the extracellular medium.

18 Claims, 22 Drawing Sheets

```
                                        MetGlnThrLeuLeuValSerSerLeuVal
  2  AATTCGGGCTCATTCCCTCATCTGCCCATCATGCAGACTCTCCTTGTGAGCTCGCTTGTG
     TTAAGCCCGAGTAAGGGAGTAGACGGGTAGTACGTCTGACAGGAACACTCGAGCGAACAC

1 ECORI, 49 SACI

ValSerLeuAlaAlaAlaLeuProHisTyrIleArgSerAsnGlyIleGluAlaSerLeu
 62  GTCTCCCTCGCTGCGGCCCTGCCACACTACATCAGGAGCAATGGCATTGAAGCCAGCCTC
     CAGAGGGAGCGACGCCGGGACGGTGTGATGTAGTCCTCGTTACCGTAACTTCGGTCGGAG

LeuThrAspProLysAspValSerGlyArgThrValAspTyrIleIleAlaGlyGlyGly
122  CTGACTGATCCCAAGGATGTCTCCGGCCGCACGGTCGACTACATCATCGCTGGTGGAGGT
     GACTGACTAGGGTTCCTACAGAGGCCGGCGTGCCAGCTGATGTAGTAGCGACCACCTCCA

145 XMA3, 155 SALI,

LeuThrGlyLeuThrThrAlaAlaArgLeuThrGluAsnProAsnIleSerValLeuVal
182  CTGACTGGACTCACCACCGCTGCTCGTCTGACGGAGAACCCCAACATCAGTGTGCTCGTC
     GACTGACCTGAGTGGTGGCGACGAGCAGACTGCCTCTTGGGGTTGTAGTCACACGAGCAG

IleGluSerGlySerThrGluSerAspArgGlyProIleIleGluAspLeuAsnThrTyr
242  ATCGAAAGTGGCTCCTACGAGTCGGACAGAGGTCCTATCATTGAGGACCTGAACACCTAC
     TAGCTTTCACCGAGGATGCTCAGCCTGTCTCCAGGATAGTAACTCCTGGACTTGTGGATG

GlyAspIlePheGlySerSerValAspHisAlaTyrGluThrValGluLeuAlaThrAsn
302  GGCGACATCTTTGGCAGCAGTGTAGACCACGCCTACGAGACCGTGGAGCTCGCTACCAAC
     CCGCTGTAGAAACCGTCGTCACATCTGGTGCGGATGCTCTGGCACCTCGAGCGATGGTTG

347 SACI,

AsnGlnThrAlaLeuIleArgSerGlyAsnGlyLeuGlyGlySerThrLeuValAsnGly
362  AATCAAACCGCGCTGATCCGCTCCGGAAATGGTCTCGGTGGCTCTACTCTAGTGAATGGT
     TTAGTTTGGCGCGACTAGGCGAGGCCTTTACCAGAGCCACCGAGATGAGATCACTTACCA

GlyThrTrpThrArgProHisLysAlaGlnValAspSerTrpGluThrValPheGlyAsn
422  GGCACCTGGACTCGCCCCCACAAGGCACAGGTTGACTCTTGGGAGACTGTCTTTGGAAAT
     CCGTGGACCTGAGCGGGGTGTTCCGTGTCCAACTGAGAACCCTCTGACAGAAACCTTTA

GluGlyTrpAsnTrpAspAsnValAlaAlaTyrSerLeuGlnAlaGluArgAlaArgAla
482  GAGGGCTGGAACTGGGACAATGTGGCCGCCTACTCCCTCCAGGCTGAGCGTGCTCGCGCA
     CTCCCGACCTTGACCCTGTTACACCGGCGGATGAGGGAGGTCCGACTCGCACGAGCGCGT
```

Protein Sequences determined from A. niger Glucose Oxidase

Sequence 1 - Nterminus

Ser Asn Gly Ile Glu Ala Ser Leu Leu Thr

Sequence 2 - tryptic fragment (Arg) Thr Val Asp Tyr Ile Ile Ala Gly Gly Gly Leu Thr Gly Leu Thr Thr Ala Sequence 3 - tryptic fragment (Arg) Leu Thr Glu Asn Pro Asn Ile Ser Val Leu Val Ile Glu Ser Gly Ser Tyr Glu Ser Asp Sequence 4 - tryptic fragment (Arg) Ile Ser Asp Ala Ser Leu (Glu,Ala) Asp (Tyr,Leu) Ala Ser Met Sequence 5 - tryptic fragment (Arg) Gly Gly Phe His (Asn) Thr Thr Ala Leu Leu Ile Gln Tyr Glu Asn Tyr Sequence 6 - CnBr fragment Met? Pro Lys Glu Met?

Sequence 7 CnBr fragment

Met Ser Ala Val Glu Asp Arg Gly Val Pro Thr Lys Lys Asp Phe Gly Gln Gly Asp Trp
Pro His Gly Val Ser Met
                        Trp

Sequence 8 CnBr fragment

Met? Phe Pro Asn Thr Leu (Leu?) Glu Asp Gln Val (Arg?)

Sequence 9 CnBr fragment

Met? Thr Val Phe Tyr Ala Met?

FIG. I

AMINO ACIDS AND NUCLEOTIDE SEQUENCES FOR GLUCOSE OXIDASE SCREENING

SEQUENCE 1

```
                        6 4 4 2 2 2 4 4 4 6 6 3 2 2 2 2 2
AMINO ACID SEQUENCE     R G G F H N T T A L L I Q Y E N Y
                                                probes 9-11--
                                                    probe 7----
                        --------probe long 2-------------
```

PROBE 7    48fold degen.17mer    TAATTCTCATATTGAAT
                                   G T   G C   T
                                                 G PROBE 9    96fold degen.20mer    TAATTCTCATATTGAATTAG
                                   G T   G C   T  C
                                                 G PROBE 10         "               TAATTCTCATATTGAATAAG
                                   G T   G C   T  G
                                                 G PROBE 11         "               TAATTCTCATATTGAATTAA
                                   G T   G C   T  C
                                                 G

PROBE LONG2    GTAGTTCTCGTACTGAATCAGCAGAGCGGTGGTGTTGTGGAAGCCGCG

```
                  1 6 4 4 2 2 6 4 4 4 4 2 2 2 4 2 4 2 4 2 4 4 6
SEQUENCE 2        M S A V E D R G V P T K K D F G Q G D P H G Y S
                                         probes 13-16---
                  ---------------probe long6----------------------
                                       .---------long7-------------
                  -----------long8------------
```

PROBE 13   128fold degen.23mer    TCNCCTTGNCCAAAATCTTTCTT
                                    C      G        G PROBE 14   128fold degen.23mer    TCNCCTTGNCCAAAATCCTTCTT
                                    C      G        G PROBE 15   128fold degen.23mer    TCNCCTTGNCCAAAATCTTTTTT
                                    C      G        G PROBE 16   128fold degen.23mer    TCNCCTTGNCCAAAATCCTTTTT
                                    C      G        G PROBE LONG6   unique 72mer
GCTCACACCGTGGGGATCACCCTGGCCGAAATCCTTCTTGGTGGGCACGCCGCGATCCTCCACAGCGCTCAT PROBE LONG7   unique 42mer
GCTCACACCGTGGGGATCACCCTGGCCGAAATCTTTCTTGGT PROBE LONG8   unique 42mer
ATCTTTCTTGGTGGGCACGCCGCGATCCTCCACAGCGCTCAT

FIG. 2

COMPARISON OF THE SEQUENCES OF PROBES LONG 6,7, AND 8.

LONG7   GCTCACACCGTGGGGATCACCCTGGCCGAAATCTTTCTTGGT
        ********************************
LONG6   GCTCACACCGTGGGGATCACCCTGGCCGAAATCCTTCTTGGTGGGCACGCCGCGATCCTCCACAGCGCTCAT
                                         ********************************
LONG8                                    ATCTTTCTTGGTGGGCACGCCGCGATCCTCCACAGGCGCTCAT

Sequence of 700 bp EcoRI fragment from cDNA clone 4.

```
        AsnSerGlyValIleGluSerGlySerTyrGluSerAspArgGlyProIleIleGluAsp
  2     AATTCGGGCGTCATCGAAAGTGGCTCCTACGAGTCGGACAGAGGTCCTATCATTGAGGAC
        TTAAGCCCGCAGTAGCTTTCACCGAGGATGCTCAGCCTGTCTCCAGGATAGTAACTCCTG

1 ECORI,

LeuAsnThrTyrGlyAspIlePheGlySerSerValAspHisAlaTyrGluThrValGlu
  62    CTGAACACCTACGGCGACATCTTTGGCAGCAGTGTAGACCACGCCTACGAGACCGTGGAG
        GACTTGTGGATGCCGCTGTAGAAACCGTCGTCACATCTGGTGCGGATGCTCTGGCACCTC

119 SACI,

LeuAlaThrAsnAsnGlnThrAlaLeuIleArgSerGlyAsnGlyLeuGlyGlySerThr
  122   CTCGCTACCAACAATCAAACCGCGCTGATCCGCTCCGGAAATGGTCTCGGTGGCTCTACT
        GAGCGATGGTTGTTAGTTTGGCGCGACTAGGCGAGGCCTTTACCAGAGCCACCGAGATGA

LeuValAsnGlyGlyThrTrpThrArgProHisLysAlaGlnValAspSerTrpGluThr
  182   CTAGTGAATGGTGGCACCTGGACTCGCCCCCACAAGGCACAGGTTGACTCTTGGGAGACT
        GATCACTTACCACCGTGGACCTGAGCGGGGGTGTTCCGTGTCCAACTGAGAACCCTCTGA

ValPheGlyAsnGluGlyTrpAsnTrpAspAsnValAlaAlaTyrSerLeuGlnAlaGlu
  242   GTCTTTGGAAATGAGGGCTGGAACTGGGACAATGTGGCCGCCTACTCCCTCCAGGCTGAG
        CAGAAACCTTTACTCCCGACCTTGACCCTGTTACACCGGCGGATGAGGGAGGTCCGACTC

ArgAlaArgAlaProAsnAlaLysGlnIleAlaAlaGlyHisTyrPheAsnAlaSerCys
  302   CGTGCTCGCGCACCAAATGCCAAACAGATCGCTGCTGGCCACTACTTCAACGCATCCTGC
        GCACGAGCGCGTGGTTTACGGTTTGTCTAGCGACGACCGGTGATGAAGTTGCGTAGGACG

337 BALI,  361 NCOI,

HisGlyValAsnGlyThrValHisAlaGlyProArgAspThrGlyAspAspTyrSerPro
  362   CATGGTGTTAATGGTACTGTCCATGCCGGACCCCGCGACACCGGCGATGACTATTCTCCC
        GTACCACAATTACCATGACAGGTACGGCCTGGGGCGCTGTGGCCGCTACTGATAAGAGGG

IleValLysAlaLeuMetSerAlaValGluAspArgGlyValProThrLysLysAspPhe
                                                 ---------------------
  422   ATCGTCAAGGCTCTCATGAGCGCTGTCGAAGACCGGGGCGTTCCCACCAAGAAAGACTTC
        TAGCAGTTCCGAGAGTACTCGCGACAGCTTCTGGCCCCGCAAGGGTGGTTCTTTCTGAAG

435 BSPH1,  472 XMNI,

GlyCysGlyAspProHisGlyValSerMetPheProAsnThrLeuHisGluAspGlnVal
        ---Gln---------------------  --------------------Leu------------
  482   GGATGCGGTGACCCCCATGGTGTGTCCATGTTCCCCAACACCTTGCACGAAGACCAAGTG
        CCTACGCCACTGGGGGTACCACACAGGTACAAGGGGTTGTGGAACGTGCTTCTGGTTCAC

488 BSTE2,  496 NCOI,

ArgSerAspAlaAlaArgGluTrpLeuLeuProAsnTyrGlnArgProAsnLeuGlnVal
        ---
  542   CGCTCCGATGCCGCTCGCGAATGGCTACTTCCCAACTACCAACGTCCCAACCTGCAAGTC
        GCGAGGCTACGGCGAGCGCTTACCGATGAAGGGTTGATGGTTGCAGGGTTGGACGTTCAG

556 NRUI,

LeuThrGlyGlnTyrValGlyLysValLeuLeuSerGlnAsnGlyThrThrProArgAla
  602   CTGACCGGACAGTATGTTGGTAAGGTGCTCCTTAGCCAGAACGGCACCACCCCTCGTGCC
        GACTGGCCTGTCATACAACCATTCCACGAGGAATCGGTCTTGCCGTGGTGGGGAGCACGG

636 BGLI,

ValGlyValGluPhe
  662   GTTGGCGTGGAATTC
        CAACCGCACCTTAAG

671 ECORI,
```

FIG. 4B

Nucleotide Sequence of Composite cDNA for Glucose Oxidase

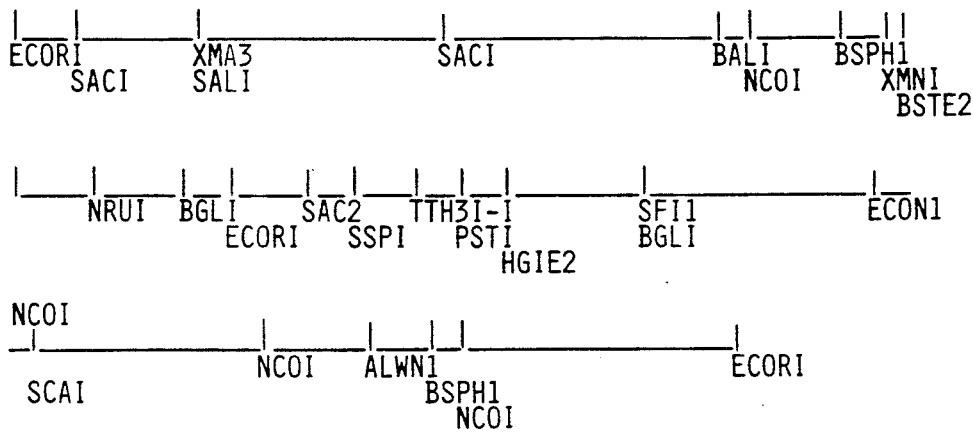

FIG. 5A

```
                                              MetGlnThrLeuLeuValSerSerLeuVal
  2  AATTCGGGCTCATTCCCTCATCTGCCCATCATGCAGACTCTCCTTGTGAGCTCGCTTGTG
     TTAAGCCCGAGTAAGGGAGTAGACGGGTAGTACGTCTGACAGGAACACTCGAGCGAACAC

1 ECORI, 49 SACI

ValSerLeuAlaAlaAlaLeuProHisTyrIleArgSerAsnGlyIleGluAlaSerLeu
 62  GTCTCCCTCGCTGCGGCCCTGCCACACTACATCAGGAGCAATGGCATTGAAGCCAGCCTC
     CAGAGGGAGCGACGCCGGGACGGTGTGATGTAGTCCTCGTTACCGTAACTTCGGTCGGAG

LeuThrAspProLysAspValSerGlyArgThrValAspTyrIleIleAlaGlyGlyGly
122  CTGACTGATCCCAAGGATGTCTCCGGCCGCACGGTCGACTACATCATCGCTGGTGGAGGT
     GACTGACTAGGGTTCCTACAGAGGCCGGCGTGCCAGCTGATGTAGTAGCGACCACCTCCA

145 XMA3, 155 SALI,

LeuThrGlyLeuThrThrAlaAlaArgLeuThrGluAsnProAsnIleSerValLeuVal
182  CTGACTGGACTCACCACCGCTGCTCGTCTGACGGAGAACCCCAACATCAGTGTGCTCGTC
     GACTGACCTGAGTGGTGGCGACGAGCAGACTGCCTCTTGGGGTTGTAGTCACACGAGCAG

IleGluSerGlySerThrGluSerAspArgGlyProIleIleGluAspLeuAsnThrTyr
242  ATCGAAAGTGGCTCCTACGAGTCGGACAGAGGTCCTATCATTGAGGACCTGAACACCTAC
     TAGCTTTCACCGAGGATGCTCAGCCTGTCTCCAGGATAGTAACTCCTGGACTTGTGGATG

GlyAspIlePheGlySerSerValAspHisAlaTyrGluThrValGluLeuAlaThrAsn
302  GGCGACATCTTTGGCAGCAGTGTAGACCACGCCTACGAGACCGTGGAGCTCGCTACCAAC
     CCGCTGTAGAAACCGTCGTCACATCTGGTGCGGATGCTCTGGCACCTCGAGCGATGGTTG

347 SACI,

AsnGlnThrAlaLeuIleArgSerGlyAsnGlyLeuGlyGlySerThrLeuValAsnGly
362  AATCAAACCGCGCTGATCCGCTCCGGAAATGGTCTCGGTGGCTCTACTCTAGTGAATGGT
     TTAGTTTGGCGCGACTAGGCGAGGCCTTTACCAGAGCCACCGAGATGAGATCACTTACCA

GlyThrTrpThrArgProHisLysAlaGlnValAspSerTrpGluThrValPheGlyAsn
422  GGCACCTGGACTCGCCCCCACAAGGCACAGGTTGACTCTTGGGAGACTGTCTTTGGAAAT
     CCGTGGACCTGAGCGGGGGTGTTCCGTGTCCAACTGAGAACCCTCTGACAGAAACCTTTA

GluGlyTrpAsnTrpAspAsnValAlaAlaTyrSerLeuGlnAlaGluArgAlaArgAla
482  GAGGGCTGGAACTGGGACAATGTGGCCGCCTACTCCCTCCAGGCTGAGCGTGCTCGCGCA
     CTCCCGACCTTGACCCTGTTACACCGGCGGATGAGGGAGGTCCGACTCGCACGAGCGCGT
```

FIG. 5B-1

```
       ProAsnAlaLysGlnIleAlaAlaGlyHisTyrPheAsnAlaSerCysHisGlyValAsn
542 CCAAATGCCAAACAGATCGCTGCTGGCCACTACTTCAACGCATCCTGCCATGGTGTTAAT
    GGTTTACGGTTTGTCTAGCGACGACCGGTGATGAAGTTGCGTAGGACGGTACCACAATTA

565 BALI, 589 NCOI,

GlyThrValHisAlaGlyProArgAspThrGlyAspAspTyrSerProIleValLysAla
602 GGTACTGTCCATGCCGGACCCCGCGACACCGGCGATGACTATTCTCCCATCGTCAAGGCT
    CCATGACAGGTACGGCCTGGGGCGCTGTGGCCGCTACTGATAAGAGGGTAGCAGTTCCGA

LeuMetSerAlaValGluAspArgGlyValProThrLysLysAspPheGlyCysGlyAsp
662 CTCATGAGCGCTGTCGAAGACCGGGGCGTTCCCACCAAGAAAGACTTCGGATGCGGTGAC
    GAGTACTCGCGACAGCTTCTGGCCCCGCAAGGGTGGTTCTTTCTGAAGCCTACGCCACTG

663 BSPH1, 700 XMNI, 716 BSTE2,

ProHisGlyValSerMetPheProAsnThrLeuHisGluAspGlnValArgSerAspAla
722 CCCCATGGTGTGTCCATGTTCCCCAACACCTTGCACGAAGACCAAGTGCGCTCCGATGCC
    GGGGTACCACACAGGTACAAGGGGTTGTGGAACGTGCTTCTGGTTCACGCGAGGCTACGG

724 NCOI

AlaArgGluTrpLeuLeuProAsnTyrGlnArgProAsnLeuGlnValLeuThrGlyGln
782 GCTCGCGAATGGCTACTTCCCAACTACCAACGTCCCAACCTGCAAGTCCTGACCGGACAG
    CGAGCGCTTACCGATGAAGGGTTGATGGTTGCAGGGTTGGACGTTCAGGACTGGCCTGTC

784 NRUI,

TyrValGlyLysValLeuLeuSerGlnAsnGlyThrThrProArgAlaValGlyValGlu
842 TATGTTGGTAAGGTGCTCCTTAGCCAGAACGGCACCACCCCTCGTGCCGTTGGCGTGGAA
    ATACAACCATTCCACGAGGAATCGGTCTTGCCGTGGTGGGGAGCACGGCAACCGCACCTT

864 BGLI, 899 ECORI,

PheGlyThrHisLysGlnAsnThrHisAsnValTyrAlaLysHisGluValLeuLeuAla
902 TTCGGCACCCACAAGGGCAACACCCACAACGTTTACGCTAAGCACGAGGTCCTCCTGGCC
    CGCCCGAGGCGACAGAGAGGGTGTTAGGAGCTTATAAGGCCATAGCCTTACTTCAGGTAG

960 SAC2,

AlaGlySerAlaValSerProThrIleLeuGluTyrSerGlyIleGlyMetLysSerIle
962 GCGGGCTCCGCTGTCTCTCCCACAATCCTCGAATATTCCGGTATCGGAATGAAGTCCATC
    CGCCCGAGGCGACAGAGAGGGTGTTAGGAGCTTATAAGGCCATAGCCTTACTTCAGGTAG

993 SSPI,

LeuGluProLeuGlyIleAspThrValValAspLeuProValGlyLeuAsnLeuGlnAsp
1022 CTGGAGCCCCTTGGTATCGACACCGTCGTTGACCTGCCCGTCGGCTTGAACCTGCAGGAC
     GACCTCGGGGAACCATAGCTGTGGCAGCAACTGGACGGGCAGCCGAACTTGGACGTCCTG

1040 TTH3I, 1073 PSTI,

GlnThrThrAlaThrValArgSerArgIleThrSerAlaGlyAlaGlyGlnGlyGlnAla
1082 CAGACCACCGCTACCGTCCGCTCCCGCATCACCTCTGCTGGTGCAGGACAGGGACAGGCC
     GTCTGGTGGCGATGGCAGGCGAGGGCGTAGTGGAGACGACCACGTCCTGTCCCTGTCCGG

1112 HGIE2,

AlaTrpPheAlaThrPheAsnGluThrPheGlyAspTyrSerGluLysAlaHisGluLeu
1142 GCTTGGTTCGCCACCTTCAACGAGACCTTTGGTGACTATTCCGAAAAGGCACACGAGCTG
     CGAACCAAGCGGTGGAAGTTGCTCTGGAAACCACTGATAAGGCTTTTCCGTGTGCTCGAC

LeuAsnThrLysLeuGluGlnTrpAlaGluGluAlaValAlaArgGlyGlyPheHisAsn
1202 CTCAACACCAAGCTGGAGCAGTGGGCCGAAGAGGCCGTCGCCCGTGGCGGATTCCACAAC
     GAGTTGTGGTTCGACCTCGTCACCCGGCTTCTCCGGCAGCGGGCACCGCCTAAGGTGTTG

1225 SFI1, 1226 BGLI,
```

FIG. 5B-2

```
       ThrThrAlaLeuLeuIleGlnTyrGluAsnTyrArgAspTrpIleValAsnHisAsnVal
1262   ACCACCGCCTTGCTCATCCAGTACGAGAACTACCGCGACTGGATTGTCAACCACAACGTC
       TGGTGGCGGAACGAGTAGGTCATGCTCTTGATGGCGCTGACCTAACAGTTGGTGTTGCAG

AlaTyrSerGluLeuPheLeuAspThrAlaGlyValAlaSerPheAspValTrpAspLeu
1322   GCGTACTCGGAACTCTTCCTCGACACTGCCGGAGTAGCCAGCTTCGATGTGTGGGACCTT
       CGCATGAGCCTTGAGAAGGAGCTGTGACGGCCTCATCGGTCGAAGCTACACACCCTGGAA

LeuProPheThrArgGlyTyrValHisIleLeuAspLysAspProTyrLeuHisHisPhe
1382   CTGCCCTTCACCCGAGGATACGTTCACATCCTCGACAAGGACCCCTACCTTCACCACTTC
       GACGGGAAGTGGGCTCCTATGCAAGTGTAGGAGCTGTTCCTGGGGATGGAAGTGGTGAAG

1411 ECON1,

AlaTyrAspProGlnTyrPheLeuAsnGluLeuAspLeuLeuGlyGlnAlaAlaAlaThr
1442   GCCTACGACCCTCAGTACTTCCTCAACGAGCTGGACCTGCTCGGTCAGGCTGCCGCTACT
       CGGATGCTGGGAGTCATGAAGGAGTTGCTCGACCTGGACGAGCCAGTCCGACGGCGATGA

1455 SCAI,

GlnLeuAlaArgAsnIleSerAsnSerGlyAlaMetGlnThrTyrPheAlaGlyGluThr
1502   CAACTGGCCCGCAACATCTCCAACTCCGGTGCCATGCAGACCTACTTCGCTGGGGAGACT
       GTTGACCGGGCGTTGTAGAGGTTGAGGCCACGGTACGTCTGGATGAAGCGACCCCTCTGA

IleProGlyAspAsnLeuAlaTyrAspAlaAspLeuSerAlaTrpThrGluThrIlePro
1562   ATCCCCGGTGATAACCTCGCGTATGATGCCGATTTGAGCGCCTGGACTGAGTACATCCCG
       TAGGGGCCACTATTGGAGCGCATACTACGGCTAAACTCGCGGACCTGACTCATGTAGGGC

TyrHisPheArgProAsnTyrHisGlyValGlyThrCysSerMetMetProLysGluMet
1622   TACCACTTCCGTCCTAACTACCATGGCGTGGGTACTTGCTCCATGATGCCGAAGGAGATG
       ATGGTGAAGGCAGGATTGATGGTACCGCACCCATGAACGAGGTACTACGGCTTCCTCTAC

1642 NCOI,

GlyGlyValValAspAsnAlaAlaArgValTyrGlyValGlnGlyLeuArgValIleAsp
1682   GGCGGTGTTGTTGATAATGCTGCCCGTGTGTATGGTGTGCAGGGACTGCGTGTCATTGAT
       CCGCCACAACAACTATTACGACGGGCACACATACCACACGTCCCTGACGCACAGTAACTA

1721 ALWN1,

GlySerIleProProThrGlnMetSerSerHisValMetThrValPheTyrAlaMetAla
1742   GGTTCTATTCCTCCTACGCAAATGTCGTCCCATGTCATGACGGTGTTCTATGCCATGGCG
       CCAAGATAAGGAGGATGCGTTTACAGCAGGGTACAGTACTGCCACAAGATACGGTACCGC

1776 BSPH1, 1794 NCOI,

LeuLysIleSerAspAlaIleLeuGluAspTyrAlaSerMetGlnOP
1802   CTAAAAATTTCGGATGCTATCTTGGAAGATTATGCTTCCATGCAGTGAGTGGTATGATGG
       GATTTTTAAAGCCTACGATAGAACCTTCTAATACGAAGGTACGTCACTCACCATACTACC

1862   GGATATGAGTGAGGATATTAGGGGATGGTACTTAGATGCTGGGGAGGTATAATCATAGAT
       CCTATACTCACTCCTATAATCCCCTACCATGAATCTACGACCCCTCCATATTAGTATCTA

1922   TGGATAGAATTGGTAGGTTACATAGACAGGTTACATGAATAGACGTTCGTTATATGTGAG
       ACCTATCTTAACCATCCAATGTATCTGTCCAATGTACTTATCTGCAAGCAATATACACTC

1982   CAGACATTACTACCAAACAAAAAAAAAAAAAAAAAACCCGAATTC
       GTCTGTAATGATGGTTTGTTTTTTTTTTTTTTTTTGGGCTTAAG

2020 ECORI,
```

FIG. 5B-3

Amino Acid Sequence of Glucose Oxidase derived from the cDNA.

```
                                            -22       -20
                                            Met Gln Thr Leu Leu Val Ser
GAATTCGGGCTCATTCCCTCATCTGCCCATC ATG CAG ACT CTC CTT GTG AGC

-10
Ser Leu Val Val Ser Leu Ala Ala Ala Leu Pro His Tyr Ile Arg
TCG CTT GTG GTC TCC CTC GCT GCG GCC CTG CCA CAC TAC ATC AGG 1                                  10
Ser Asn Gly Ile Glu Ala Ser Leu Leu Thr Asp Pro Lys Asp Val
AGC AAT GGC ATT GAA GCC AGC CTC CTG ACT GAT CCC AAG GAT GTC 20                                      30
Ser Gly Arg Thr Val Asp Tyr Ile Ile Ala Gly Gly Glu Leu Thr
TCC GGC CGC ACG GTC GAC TAC ATC ATC GCT GGT GGA GGT CTG ACT

40
Gly Leu Thr Thr Ala Ala Arg Leu Thr Glu Asn Pro Asn Ile Ser
GGA CTC ACC ACC GCT GCT CGT CTG ACG GAG AAC CCC AAC ATC AGT 50                                          60
Val Leu Val Ile Glu Ser Gly Ser Tyr Glu Ser Asp Arg Gly Pro
GTG CTC GTC ATC GAA AGT GGC TCC TAC GAG TCG GAC AGA GGT CCT

70
Ile Ile Glu Asp Leu Asn Thr Tyr Gly Asp Ile Phe Gly Ser Ser
ATC ATT GAG GAC CTG AAC ACC TAC GGC GAC ATC TTT GGC AGC AGT 80                                          90
Val Asp His Ala Tyr Glu Thr Val Glu Leu Ala Thr Asn Asn Gln
GTA GAC CAC GCC TAC GAG ACC GTG GAG CTC GCT ACC AAC AAT CAA

100
Thr Ala Leu Ile Arg Ser Gly Asn Gly Leu Gly Gly Ser Thr Leu
ACC GCG CTG ATC CGC TCC GGA AAT GGT CTC GGT GGC TCT ACT CTA 110                                       120
Val Asn Gly Gly Thr Trp Thr Arg Pro His Lys Ala Gln Val Asp
GTG AAT GGT GGC ACC TGG ACT CGC CCC CAC AAG GCA CAG GTT GAC

130
Ser Trp Glu Thr Val Phe Gly Asn Glu Gly Trp Asn Trp Asp Asn
TCT TGG GAG ACT GTC TTT GGA AAT GAG GGC TGG AAC TGG GAC AAT 140                                       150
Val Ala Ala Tyr Ser Leu Gln Ala Glu Arg Ala Arg Ala Pro Asn
GTG GCC GCC TAC TCC CTC CAG GCT GAG CGT GCT CGC GCA CCA AAT

160
Ala Lys Gln Ile Ala Ala Gly His Tyr Phe Asn Ala Ser Cys His
GCC AAA CAG ATC GCT GCT GGC CAC TAC TTC AAC GCA TCC TGC CAT 170                                       180
Gly Val Asn Gly Thr Val His Ala Gly Pro Arg Asp Thr Gly Asp
GGT GTT AAT GGT ACT GTC CAT GCC GGA CCC CGC GAC ACC GGC GAT

190
Asp Tyr Ser Pro Ile Val Lys Ala Leu Met Ser Ala Val Glu Asp
GAC TAT TCT CCC ATC GTC AAG GCT CTC ATG AGC GCT GTC GAA GAC
```

FIG. 6-1

```
             200                                          210
Arg Gly Val Pro Thr Lys Lys Asp Phe Gly Cys Gly Asp Pro His
------------------------------------------Gln----------------
CGG GGC GTT CCC ACC AAG AAA GAC TTC GGA TGC GGT GAC CCC CAT

220
Gly Val Ser Met Phe Pro Asn Thr Leu His Glu Asp Gln Val Arg
------------------------------------Leu---------------------
GGT GTG TCC ATG TTC CCC AAC ACC TTG CAC GAA GAC CAA GTG CGC 230                                          240
Ser Asp Ala Ala Arg Glu Trp Leu Leu Pro Asn Tyr Gln Arg Pro
TCC GAT GCC GCT CGC GAA TGG CTA CTT CCC AAC TAC CAA CGT CCC

250
Asn Leu Gln Val Leu Thr Gly Gln Tyr Val Gly Lys Val Leu Leu
AAC CTG CAA GTC CTG ACC GGA CAG TAT GTT GGT AAG GTG CTC CTT 260                                          270
Ser Gln Asn Gly Thr Thr Pro Arg Ala Val Gly Val Glu Phe Gly
AGC CAG AAC GGC ACC ACC CCT CGT GCC GTT GGC GTG GAA TTC GGC

280
Thr His Lys Gly Asn Thr His Asn Val Tyr Ala Lys His Glu Val
ACC CAC AAG GGC AAC ACC CAC AAC GTT TAC GCT AAG CAC GAG GTC 290                                          300
Leu Leu Ala Ala Gly Ser Ala Val Ser Pro Thr Ile Leu Glu Tyr
CTC CTG GCC GCG GGC TCC GCT GTC TCT CCC ACA ATC CTC GAA TAT

310
Ser Gly Ile Gly Met Lys Ser Ile Leu Glu Pro Leu Gly Ile Asp
TCC GGT ATC GGA ATG AAG TCC ATC CTG GAG CCC CTT GGT ATC GAC 320                                          330
Thr Val Val Asp Leu Pro Val Gly Leu Asn Leu Gln Asp Gln Thr
ACC GTC GTT GAC CTG CCC GTC GGC TTG AAC CTG CAG GAC CAG ACC

340
Thr Ala Thr Val Arg Ser Arg Ile Thr Ser Ala Gly Ala Gly Gln
ACC GCT ACC GTC CGC TCC CGC ATC ACC TCT GCT GGT GCA GGA CAG 350                                          360
Gly Gln Ala Ala Trp Phe Ala Thr Phe Asn Glu Thr Phe Gly Asp
GGA CAG GCC GCT TGG TTC GCC ACC TTC AAC GAG ACC TTT GGT GAC

370
Tyr Ser Glu Lys Ala His Glu Leu Leu Asn Thr Lys Leu Glu Gln
TAT TCC GAA AAG GCA CAC GAG CTG CTC AAC ACC AAG CTG GAG CAG 380                                          390
Trp Ala Glu Glu Ala Val Ala Arg Gly Gly Phe His Asn Thr Thr
-----------------------------------------------------------
TGG GCC GAA GAG GCC GTC GCC CGT GGC GGA TTC CAC AAC ACC ACC

400
Ala Leu Leu Ile Gln Tyr Glu Asn Tyr Arg Asp Trp Ile Val Asn
-----------------------------------------------------------
GCC TTG CTC ATC CAG TAC GAG AAC TAC CGC GAC TGG ATT GTC AAC 410                                          420
His Asn Val Ala Tyr Ser Glu Leu Phe Leu Asp Thr Ala Gly Val
CAC AAC GTC GCG TAC TCG GAA CTC TTC CTC GAC ACT GCC GGA GTA
```

FIG.6-2

```
                              430
Ala Ser Phe Asp Val Trp Asp Leu Leu Pro Phe Thr Arg Gly Tyr
GCC AGC TTC GAT GTG TGG GAC CTT CTG CCC TTC ACC CGA GGA TAC
                440                              450
Val His Ile Leu Asp Lys Asp Pro Tyr Leu His His Phe Ala Tyr
GTT CAC ATC CTC GAC AAG GAC CCC TAC CTT CAC CAC TTC GCC TAC
                                 460
Asp Pro Gln Tyr Phe Leu Asn Glu Leu Asp Leu Leu Gly Gln Ala
GAC CCT CAG TAC TTC CTC AAC GAG CTG GAC CTG CTC GGT CAG GCT
                470                                      480
Ala Ala Thr Gln Leu Ala Arg Asn Ile Ser Asn Ser Gly Ala Met
GCC GCT ACT CAA CTG GCC CGC AAC ATC TCC AAC TCC GGT GCC ATG
                                 490
Gln Thr Tyr Phe Ala Gly Glu Thr Ile Pro Gly Asp Asn Leu Ala
CAG ACC TAC TTC GCT GGG GAG ACT ATC CCC GGT GAT AAC CTC GCG
                500                                      510
Tyr Asp Ala Asp Leu Ser Ala Trp Thr Glu Tyr Ile Pro Tyr His
TAT GAT GCC GAT TTG AGC GCC TGG ACT GAG TAC ATC CCG TAC CAC
                                 520
Phe Arg Pro Asn Tyr His Gly Val Gly Thr Cys Ser Met Met Pro
                                                 -------
TTC CGT CCT AAC TAC CAT GGC GTG GGT ACT TGC TCC ATG ATG CCG
                530                                      540
Lys Glu Met Gly Gly Val Val Asp Asn Ala·Ala Arg Val Tyr Gly
-----------
AAG GAG ATG GGC GGT GTT GTT GAT AAT GCT GCC CGT GTG TAT GGT
                                 550
Val Gln Gly Leu Arg Val Ile Asp Gly Ser Ile Pro Pro Thr Gln
GTG CAG GGA CTG CGT GTC ATT GAT GGT TCT ATT CCT CCT ACG CAA
                560                                      570
Met Ser Ser His Val Met Thr Val Ph eTyr Ala Met Ala Leu Lys
                                                         Arg
ATG TCG TCC CAT GTC ATG ACG GTG TTC TAT GCC ATG GCG CTA AAA 580         583
Ile Ser Asp Ala Ile Leu Glu Asp Tyr Ala Ser Met Gln OP
-----------------Ser---------------------------
ATT TCG GAT GCT ATC TTG GAA GAT TAT GCT TCC ATG CAG TGA GTGGTA
TGATGGGGATATGAGTGAGGATATTAGGGGATGGTACTTAGATGCTGGGGAGGTATAATC
ATAGATTGGATAGAATTGGTAGGTTACATAGACAGGTTACATGAATAGACGTTCGTTATA
TGTGAGCAGACATTACTACCAAACAAAAAAAAAAAAAAAAACCCGAATTC

Translated Mol. Weight = 65679.50 (including signal peptide)
```

FIG.6-3

Codon usage:

| | | | |
|---|---|---|---|
| 3/UUU/phe | 6/UCU/ser | 8/UAU/tyr | 0/UGU/cys |
| 15/UUC/phe | 18/UCC/ser | 20/UAC/tyr | 3/UGC/cys |
| 0/UUA/leu | 0/UCA/ser | 0/UAA/OC | 1/UGA/OP |
| 5/UUG/leu | 5/UCG/ser | 0/UAG/AM | 10/UGG/trp |
| 7/CUU/leu | 6/CCU/pro | 5/CAU/his | 8/CGU/arg |
| 20/CUC/leu | 16/CCC/pro | 15/CAC/his | 11/CGC/arg |
| 3/CUA/leu | 2/CCA/pro | 6/CAA/gln | 1/CGA/arg |
| 19/CUG/leu | 2/CCG/pro | 17/CAG/gln | 1/CGG/arg |
| 6/AUU/ile | 12/ACU/thr | 9/AAU/asn | 3/AGU/ser |
| 21/AUC/ile | 27/ACC/thr | 24/AAC/asn | 8/AGC/ser |
| 0/AUA/ile | 1/ACA/thr | 3/AAA/lys | 1/AGA/arg |
| 12/AUG/met | 4/ACG/thr | 12/AAG/lys | 1/AGG/arg |
| 10/GUU/val | 23/GCU/ala | 12/GAU/asp | 22/GGU/gly |
| 19/GUC/val | 26/GCC/ala | 24/GAC/asp | 20/GGC/gly |
| 2/GUA/val | 5/GCA/ala | 11/GAA/glu | 14/GGA/gly |
| 15/GUG/val | 6/GCG/ala | 19/GAG/glu | 1/GGG/gly |

FIG. 6-4

Sequence of the Region 5' to the Glucose Oxidase Gene.

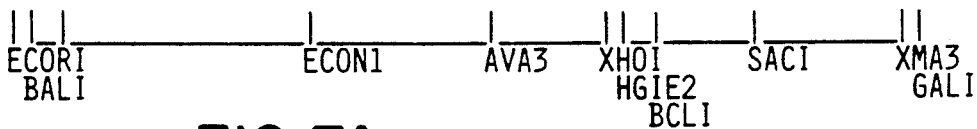

FIG. 7A

```
  3 ATTCGGTATTCTCGGCATGGCCAAAGTCGGTATCCCTTGGCGCCACGATGATTTGCGTCC
    TAAGCCATAAGAGCCGTACCGGTTTCAGCCATAGGGAACCGCGGTGCTACTAAACGCAGG

1 ECORI, 20 BALI, 41 NARI,

63 AGGATTCGTATAGTTCCTCGTCCACGAGCTGCCTACCGTCAGCGTGAGGCAGTGAGCTAA
    TCCTAAGCATATCAAGGAGCAGGTGCTCGACGGATGGCAGTCGCACTCCGTCACTCGATT

123 TATGGGGCCAATAAGCCACTACGAGGATGACATGGCCTCTACAGAACGAGAGACGCAGAG
    ATACCCCGGTTATTCGGTGATGCTCCTACTGTACCGGAGATGTCTTGCTCTCTGCGTCTC

183 GATCAGGACGCCAATCCTGCGCTCCACCTGTCTAAGGATTCGCTTTTGGACTATCCAGGG
    CTAGTCCTGCCGTTAGGACGCGAGGTGGACAGATTCCTAAGCGAAAACCTGATAGGTCCC

209 ECON1,

243 ATTATGGCTTCGGATTATTGTATTCGGGATACCGACGGCTGAGCACACGGAGGATGAGGT
    TAATACCGAAGCCTAATAACATAAGCCCTATGGCTGCCGACTCGTGTGCCTCCTACTCCA

303 TCAGCTCACGGCCCCTATCAGTATGCATTATGAGGATGGCTTCTTGGAAAGCAGAGGAAT
    AGTCGAGTGCCGGGGATAGTCATACGTAATACTCCTACCGAAGAACCTTTCGTCTCCTTA

325 AVA3,

363 TGGATTATCGAACAAGTTGGTTCTGGACCATTGACTCGAGCGTATAAGTAACCTCGTTCG
    ACCTAATAGCTTGTTCAACCAAGACCTGGTAACTGAGCTCGCATATTCATTGGAGCAAGC

397 XHOI, 413 HGIE2,

423 GTCCTCCTGTCACCTTCTGATCAGCAACCAGCCTTTCCTCTCTCATTCCCTCATCTGCCC
    CAGGAGGACAGTGGAAGACTAGTCGTTGGTCGGAAAGGAGAGAGTAAGGGAGTAGACGGG

440 BCLI,

MetGlnThrLeuLeuValSerSerLeuValValSerLeuAlaAlaAlaLeuProHis
433 ATCATGCAGACTCTCCTTGTGAGCTCGCTTGTGGTCTCCCTCGCTGCGGCCCTGCCACAC
    TAGTACGTCTGAGAGGAACACTCGAGCGAACACCAGAGGGAGCGACGCCGGGACGGTGTG

503 SACI,

TyrIleArgSerAsnGlyIleGluAlaSerLeuLeuThrAspProLysAspValSerGly
543 TACATCAGGAGCAATGGCATTGAAGCCAGCCTCCTGACTGATCCCAAGGATGTCTCCGGC
    ATGTAGTCCTCGTTACCGTAACTTCGGTCGGAGGACTGACTAGGGTTCCTACAGAGGCCG

599 XMA3,

ArgThrValAsp
603 CGCACGGTCGAC
    GCGTGCCAGCTG

609 SALI,
```

FIG. 7B

Partial Sequence of a fragment of clone pBRA11

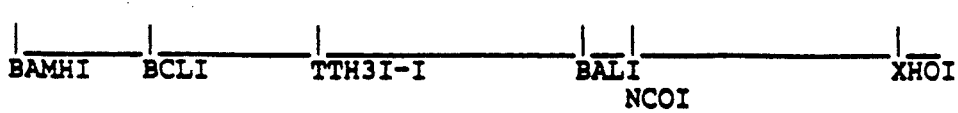

```
     AspProAsnAlaTyrGlyGlnIlePheGlyThrThrValAspGlnAsnTyrLeuThrVal
  2  GATCCAAATGCTTATGGACAAATCTTTGGCACCACTGTTGACCAGAACTACCTCACCGTT
     CTAGGTTTACGAATACCTGTTTAGAAACCGTGGTGACAACTGGTCTTGATGGAGTGGCAA

1 BAMHI,

ProLeuIleAsnAsnArgThrAsnAsnIleLysAlaGlyLysGlyLeuGlyGlySerThr
 62  CCCCTGATCAACAACCGCACGAACAATATCAAGGCCGGTAAAGGTCTTGGAGGATCAACC
     GGGGACTAGTTGTTGGCGTGCTTGTTATAGTTCCGGCCATTTCCAGAACCTCCTAGTTGG

66 BCLI,

LeuIleAsnGlyAspSerTrpThrArgProAspLysValGlnIleAspSerTrpGluLys
122  TTGATAAACGGTGACTCCTGGACTCGCCCAGACAAAGTCCAGATTGATTCTTGGGAGAAG
     AACTATTTGCCACTGAGGACCTGAGCGGGTCTGTTTCAGGTCTAACTAAGAACCCTCTTC

152 TTH3I,

ValPheGlyLeuGluGlyTrpAsnTrpAspAsnMetPheGluTyrMetLysLysAlaGlu
182  GTCTTTGGACTGGAAGGTTGGAATTGGGACAACATGTTCGAGTACATGAAGAAGGCCGAG
     CAGAAACCTGACCTTCCAACCTTAACCCTGTTGTACAAGCTCATGTACTTCTTCCGGCTC

AlaAlaArgThrProThrAlaAlaGlnLeuAlaSerGlyHisSerPheAsnAlaThrCys
242  GCTGCACGTACCCCTACTGCTGCTCAGCTTGCGTCTGGCCACTCCTTCAATGCTACCTGC
     CGACGTGCATGGGGATGACGACGAGTCGAACGCAGACCGGTGAGGAAGTTACGATGGACG

277 BALI, 301 NCOI,

HisGlyThrAsnGlyThrValGlnSerGlyAlaArgAspLysProAlaLeuValSerTyr
302  CATGGAACCAACGGTACTGTTCAATCCGGAGCCCGTGACAAGCCAGCCTTGGTCTCCTAT
     GTACCTTGGTTGCCATGACAAGTTAGGCCTCGGGCACTGTTCGGTCGGAACCAGAGGATA

TyrGluGlyProTyrGluHisArgLeuAlaLeuGlyValProTyrSerLysThrPheSer
362  TATGAAGGCCCTTATGAACACCGTCTCGCCCTTGGTGTCCCGTACAGCAAGACTTTCTCT
     ATACTTCCGGGAATACTTGTGGCAGAGCGGGAACCACAGGGCATGTCGTTCTGAAAGAGA

ValValIleLeuGluValSerLeu
422  GTGGTCATCCTCGAGGTGTCTCTATG
     CACCAGTAGGAGCTCCACAGAGATAC

431 XHOI,

ALIGNMENT of A. niger and P. amagasakiense Glucose oxidase Sequences

```
  0    sngieaslltdpkdvsgrtvdyiiagggltglttaarltenpnisvlviesgsyesdrgpiieDlNt [Y
  0                                                                 DpNa[Y 68    G] d [IFG] ss [VD] haYe [TV] eLat [NN] qTalIrsGn [GLGGSTL] v [NG] gt [
  5    G] q [IFG] tt [VD] qnYl [TV] pLi. [NN] rTnnIkaGk [GLGGSTL] i [NG] ds [

110    WTRP] hKaQv [DSWE] t [VFG] n [EGWNWDN] vaayslq [AE] r [AR] aPnAkQiAa [
 46    WTRP] dKvQi [DSWE] k [VFG] l [EGWNWDN] mfeymkk [AE] a [AR] tPtAaQlAs [

156    GH] y [FNA] s [CHG] v [NGTV] haGp [RD] tgddySpivkalmsavedr [GVP] tkKdF
 92    GH] s [FNA] t [CHG] t [NGTV] qsGa [RD] kpalvSyyegpyehrlal. [GVP] ysKtF 204    gcgdphg [VS] mfpntlh

POLYNUCLEOTIDE SEQUENCE FOR PRODUCTION OF GLUCOSE OXIDASE IN RECOMBINANT SYSTEMS

CROSS-REFERENCE TO RELATED APPLICATIONS

This application is a continuation of application Ser. No. 07/366,377 filed, Jun. 19, 1989, now U.S. Pat. No. 5,094,951, which is a continuation-in-part of copending application U.S. Ser. No. 209,530, filed Jun. 21, 1988, now abandoned.

TECHNICAL FIELD

The present invention relates to the use of recombinant DNA technology to produce proteins for industrial use. More particularly, the present invention is directed to recombinant vectors containing a polynucleotide derived from fungi, which encodes glucose oxidase, and to the production of glucose oxidase by host cells transformed with recombinant expression vectors containing the polynucleotide.

BACKGROUND

The techniques of genetic engineering have been successfully applied to the pharmaceutical industry, resulting in a number of novel products. Increasingly, it has become apparent that the same technologies can be applied on a large scale to the production of enzymes of value to other industries. The benefits of achieving commercially useful processes through genetic engineering are expected to include cost savings in enzyme production, productions of enzymes in organisms generally recognized as safe which are suitable for food products, and specific genetic modifications at the genomic level to improve enzyme properties, such as thermal stability and performance characteristics, as well as those which would increase the ease with which the enzyme can be purified.

Glucose oxidase is the enzyme which catalyzes the oxidation of glucose to gluconic acid with the concomitant production of hydrogen peroxide. The enzyme has many industrial uses, including its use in desugaring eggs, in the removal of oxygen from beverages, moist food products, flavors, and hermetically sealed food packages, and in the detection and estimation of glucose in industrial solutions, and in body fluids such as blood and urine.

Glucose oxidase was first isolated from cells of *Aspergillus niger* by Muller [Biocehmische Zeitschrift (1928), 199, 136-170 and (1931), 232, 423-424], and was also extracted from *A. niger* by Franke and Deffner [Annalen der Chemie (1939), 541, 117-150]. The production of glucose oxidase from cells of species of *Penicillium chrysogenum, Penicillium glaucum, Pencillium purpurogenum, Aspergillus niger* and *Aspergillus fumaricus*, has been described by Baker, in U.S. Pat. No. 2,482,724. A method for preparing glucose oxidase in which glucose oxidaseproducing strains of the genera Aspergillus and Penicillium are cultivated in medium having a low carbohydrate content is described in U.S. Pat. No. 3,701,715. The enzyme from *Aspergillus niger* (*A. niger*) has been purified to a high degree of purity, and reportedly has a molecular weight of approximately 150,000, an isoelectric point of 4.2, and a flavin adenine dinucleotide (FAD) content of 2 FAD per mole. Pazur and Kleppe (1964), Biochemistry 3, 578-583. The amino acid composition of the enzyme from *A. niger*, as well as its identity as a glycoprotein are also known. Pazur et al. (1965), Arch. Biochem. Biophys. 111, 351-357. However, neither the amino acid sequence of glucose oxidase, nor the nucleotide sequence encoding it are known.

A problem with utilizing glucose oxidase isolated from its native source is that the organisms which produce the enzyme may have contaminants which are deleterious for certain uses of the desired protein. For example, glucose oxidase is used for the commercial preparation of foodstuffs. However, *A. niger*, which is a major source of commercially prepared enzyme, is highly allergenic, and is not approved for use in food. Moreover, stringent purification procedures may be relatively expensive since glucose oxidase is primarily an intracellular enzyme. These problems could be solved by producing glucose oxidase in recombinant systems.

Fungal enzymes have been expressed from recombinant vectors. Glucoamylase from Aspergillus [Innis et al (1985), Science 228, 21-26] and endoglucanase I from *Trichoderma reesei* [Van Arsdell et al (1987), Biotechnology 5, 60-64] have been expressed in *Saccharomyces cerevisiae*.

References Cited in Following Text

Barr et al. (1986), Biotechniques 4, 428.
Boel et al. (1984), Embo J. 3, 1581.
Botstein et al. (1979), Gene 8:17.
Broach (1981), in MOLECULAR BIOLOGY OF THE YEAST SACCHAROMYCES, Vol. 1, p.445.
Chang et al. (1977), Nature 198, 1056.
Chirgwin et al. (1979), Biochemistry 18, 5294.
Clewell et al. (1969), Proc. Natl. Acad. Sci. USA 62, 1159.
Clewell et al. (1972), J. Bacteriol. 110, 667.
Cohen (1972), Proc. Natl. Acad. Sci. USA 69, 2110.
De Boer et al. (1983), Proc. Natl. Acad. Sci. USA 292, 128.
Edge (1981), Nature 292, 756.
Ehrhart and Hollenberg (1983), J. Bacteriol. 156, 625.
Gate, ed. (1984), OLIGONUCLEOTIDE SYNTHESIS
Glisin (1974), Biochemistry 13, 2633.
Glover, ed. (1985), DNA CLONING: VOL. 1 and VOL. 2.
Goeddel et al. (1980), Nucleic Acids Res. 8, 4057.
Graham and Van der Eb (1978), Virology 52, 546.
Grunstein and Hogness (1975), Proc. Natl. Acad. Sci. USA 73, 6961.
Hames & Higgins, eds. (1985), NUCLEIC ACID HYBRIDIZATION Hammerling et al. (1981) MONOCLONAL ANTIBODIES AND T-CELL HYBRIDOMAS.
Hess et al. (1968), J. Adv. Enzym Reg. 7, 149.
Hinnen et al. (1978), Proc. Natl. Acad. Sci. USA 75, 1929.
Hitzeman (1980), J. Biol. chem. 255, 2073.
Holland (1978), Biochemistry 17, 4900.
Holland (1981) J. Biol. chem. 256, 1385.
Huynh et al. (1985), DNA CLONING, A PRACTICAL APPROACH (D.M. Glover, ed., IRL Press, pp. 47-78).
Innis et al. (1985), Science 228, 21.
Jay et al. (1984), J. Biol. Chem. 259, 6311.
Kelley and Reddy (1986), J. Bact. 166, 269.

Kennet et al. (1980), MONOCLONAL ANTIBODIES.
Laemmli (1970), Nature 227, 680.
Lei et al. (1987), J. Bacteriol 169, 1987.
Malikkides and Weiland (1982), Biotech. Bioeng. 24, 1911.
Maniatis et al. (1982), MOLECULAR CLONING: A LABORATORY MANUAL
Maxam et al. (1980), Methods in Enzymology 65, 499.
Messing et al. (1981), Nucleic Acids Res. 9, 309.
Messing (1983), Methods in Enzymology 101, 20–37
METHODS IN ENZYMOLOGY (Academic Press, Inc.)
Miller and Calos, eds. (1987), GENE TRANSFER VECTORS FOR MAMMALIAN CELLS (J. H. Miller and M. P. Calos, eds., Cold Spring Harbor Laboratory)
Nambair et al. (1984), Science 223, 1299
Pazur and Kleppe (1964), Biochem. 3, 578.
Perbal (1984), A PRACTICAL GUIDE TO MOLECULAR CLONING.
Poznansky et al. (1980) in DRUG DELIVERY SYSTEMS (R. L. Juliano, ed., Oxford, N.Y. 1980).
Poznansky et al. (1984), Phar. Revs. 36, 277.
Sanger et al. (1977), Proc. Natl. Acad. Sci. USA 74, 5463.
Schreier et al. (1980), HYBRIDOMA TECHNIQUES.
Scopes (1987), PROTEIN PURIFICATION, PRINCIPLES AND PRACTICE, 2nd edition (Springer-Verlag).
Shimatake et al. (1981), Nature 292, 128.
Taylor et al. (1985), Nucl. Acids Res. 13, 8749.
Travis et al. (1985), J. Biol. Chem. 260, 4384–4389.
Urdea et al. (1983), Proc. Natl. Acad. Sci. USA 80, 7461.
Warner (1984), DNA 3, 401.
Wood et al. (1985), Proc. Natl. Acad. Sci. USA 82, 1585.
Zoller (1982), Nucleic Acids Res. 10, 6487.

DISCLOSURE OF THE INVENTION

The present invention provides a cDNA sequence encoding glucose oxidase (GO) from a fungal source of the genus Aspergillus, and more particularly from *A. niger*. Knowledge of this sequence allows the expression in recombinant systems of polypeptides substantially similar to GO, including GO, analogs of GO, and fragments of GO. Surprisingly, relatively large amounts of the enzyme are produced in and secreted from yeast cells, when the cells are transformed with an expression vector encoding GO, and grown under conditions allowing expression of the enzyme. The secretion may be under the control of either yeast secretory sequences, or the prepro sequence of GO encoded in *A. niger*.

The cDNA sequence provided herein also allows for the isolation of GO-encoding sequences from other sources, which can also be used for the production of recombinant GO. These other sources may be of any origin wherein the enzyme is naturally encoded, but will be particularly fungal sources, wherein the GO-encoding sequence contains at least 8 base pairs, preferably 20 base pairs, and even more preferably at least 40 base pairs which are highly homologous (i.e., have at most a one base mismatch in complementary sequences) to a comparable sequence in FIG. 5B. Alternatively, the GO isolated from the source other than *A. niger* may have a sequence of at least about 4 amino acids, homologous to that of the *A. niger* GO sequence encoded in the cDNA sequence in FIG. 5B.

The polypeptides expressed in yeast transformed with expression vectors encoding the GO cDNA have been examined, and the surprising result obtained that the products were hyperglycosylated, and that the hyperglycosylation of the recombinantly produced polypeptide has little or no effect on enzymatic activity, as compared to native GO, but that the recombinant product exhibited increased thermostability.

Another surprising result is that removal of the carbohydrate residues from both recombinantly produced GO and native GO apparently does not inhibit enzymatic activity.

Still another surprising result is that although native GO is present in *A. niger* in relatively large amounts, the mRNA encoding it is relatively rare in *A. niger* cells during log-phase growth.

Yet another surprising result is that an analog of GO, i.e., a mutein, exhibits increased thermostability relative to the native molecule from *A. niger* and to its recombinant counterpart expressed in yeast.

Accordingly, one aspect of the invention is a recombinant vector comprising a polynucleotide sequence encoding a polypeptide substantially similar to glucose oxidase (GO), essentially free of other vectors that do not encode GO.

Another aspect of the invention is a host cell transformed with a recombinant polynucleotide comprising a sequence encoding a polypeptide substantially similar to GO.

Yet another aspect of the invention is non-native polypeptide substantially similar to GO.

The invention includes a method of producing a recombinant polypeptide substantially similar to GO, comprising:

(a) providing a population of transformed cells containing a recombinant vector which is comprised of a coding sequence for a polypeptide substantially similar to GO operationally linked to sequences allowing expression of said coding sequence in said cells;

(b) growing said population of transformed cells under conditions whereby said polypeptide substantially similar to GO is expressed; and (c) recovering said polypeptide substantially similar to GO.

BRIEF DESCRIPTION OF THE DRAWINGS

FIG. 1 shows the amino acid sequences of fragments of native GO from *A. niger*.

FIG. 2 shows the oligonucleotide probes designed from the amino acid sequence of native GO from *A. niger* for screening for sequences encoding GO.

FIG. 4B shows the cDNA sequence of GO in clone 4, the derived amino acid sequence, and the location of restriction enzyme sites.

FIG. 5A shows a restriction enzyme map of a composite cDNA encoding GO from *A. niger*.

FIG. 5B (parts 1-3) shows the cDNA sequence of a composite cDNA encoding GO from *A. niger*, the derived amino acid sequence, and the location of restriction enzyme sites.

FIG. 6 (parts 1-4) shows the identity of fragments of native GO from *A. niger* with sequences derived from the composite cDNA shown in FIG. 5B, and the codon usage.

FIG. 7A shows a restriction enzyme map of the region 5' to the GO gene in *A. niger.*

FIG. 7B shows the nucleotide sequence of the region 5' to the GO gene in *A. niger.*

FIG. 16 shows the partial nucleotide sequence of a segment of the genome of *P. amagasakiense* in clone pBRpGOXA11; also shown are the amino acids and the restriction enzyme sites encoded therein.

FIG. 17 shows a comparison of the amino acids encoded in the fragment derived from the *P. amagasakiense* genome insert in pBRpGOXA11 with the amino acid sequence of *A. niger* GO encoded in the nucleotide sequence shown in FIG. 5B.

MODES FOR CARRYING OUT THE INVENTION

I. Definitions

Figures 3, 4A:
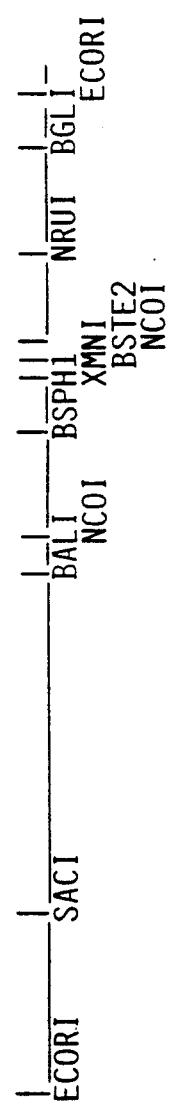
FIG. 3 shows the 42-mer probes Long 7 and long 8, and their relationship to the probe Long 6.
FIG. 4A shows a restriction map of the GO cDNA isolated from clone 4.

In describing the present invention, the following terminology will be used in accordance with the definitions set out below.

As used herein, the term "glucose oxidase" refers to a polypeptide which catalyzes the oxidation of glucose to gluconic acid with the concomitant production of hydrogen peroxide. Procedures for determining glucose oxidase activity are known in the art, and include, for example, a colorimetric assay in which glucose oxidase activity is coupled to a peroxidase-o-dianisidine system. This type of assay system is discussed in Example IV.

The term "recombinant polynucleotide" as used herein to characterize a polynucleotide useful for the production of GO intends a polynucleotide of genomic, cDNA, semisynthetic, or synthetic origin which, by virtue of its origin or manipulation: (1) is not associated with all or a portion of the polynucleotide with which it is associated in nature, and/or (2) is linked to a polynucleotide other than that to which it is linked in nature, or (3) does not occur in nature.

The term "polynucleotide" as used herein refers to a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modified, for example by methylation, phosphorylation, and/or by capping, and unmodified forms of the polynucleotide.

A "replicon" is any genetic element, e.g., a plasmid, a chromosome, a virus, that behaves as an autonomous unit of polynucleotide replication within a cell; i.e., capable of replication under its own control.

A "vector" is a replicon in which another polynucleotide segment is attached, so as to bring about the replication and/or expression of the attached segment.

"Control sequence" refers to polynucleotide sequences which are necessary to effect the expression and/or secretion of coding sequences to which they are ligated. The nature of such control sequences differs depending upon the host organism; in prokaryotes, such control sequences generally include promoter, ribosomal binding site, and terminators; in eukaryotes, generally such control sequences include promoters, terminators and, in some instances enhancers. In addition, in both prokaryotes and eukaryotes, leader sequences control the secretion of the expressed polypeptide from the host cell. The term "control sequences" is intended to include, at a minimum, all components whose presence is necessary for expression, and may also include additional components whose presence is advantageous, for example, leader sequences.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" is a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences.

"Recombinant host cells", "host cells", "cells", "cell lines", "cell cultures", and other terms denoting microorganisms or higher eukaryotic cell lines cultured as unicellular entities, are used interchangeably, and refer to cells which can be, or have been, used as recipients for recombinant vector or other transfer polynucleotides, and include the progeny of the original cell which has been transfected. It is understood that the progeny of a single parental cell may not necessarily be completely identical in morphology or in genomic or total DNA complement as the original parent, due to accidental or deliberate mutation. Progeny of the parental cell which are sufficiently similar to the parent can be characterized by the relevant property, such as the presence of a nucleotide sequence encoding a desired peptide, are included in the progeny intended by this definition, and are covered by the above terms.

"Transformation", as used herein, refers to the insertion of an exogenous polynucleotide into a host cell, irrespective of the method used for insertion, for example, direct uptake, transduction, or f-mating. The exogenous polynucleotide may be maintained as a non-integrated vector, for example, a plasmid, or alternatively, may be integrated into the host genome.

As used herein, the term "polypeptide" refers to the amino acid product of a sequence encoded within a genome, and does not refer to a specific length of the product, thus, peptides, oligopeptides, and proteins are included within the definition of polypeptide. This term also does not refer to post-expression modifications of the polypeptide, for example, glycosylations, acetylations, phosphorylations, sialylations, and the like.

The term "polypeptide substantially similar to glucose oxidase or GO" refers to non-naturally occurring forms of GO, for example, with respect to post-translational modifications including glycosylations, phosphorylations, and the like, but which have the same amino acid sequence as native GO, analogs of GO, fragments of GO, analogs of fragments of GO, and fusion polypeptides wherein GO or an analog or fragment is fused to another polypeptide with which it is not normally fused in nature. An "analog of GO" or an "analog of a fragment of GO" is one in which the homology to native GO or from the comparable fragment is greater than about 70% with respect to amino acid sequence, and preferably is greater than about 80%. Also included within this term are analogs in which one or more of the naturally occurring amino acids is substituted by a non-naturally occurring substance which is known in the art, for example, a non-naturally occurring amino acid, etc. Polypeptides which are fragments or analogs of GO may or may not be "active". An "active" polypeptide is one which, with the appropriate cofactors and substrates, catalyze the reaction normally catalyzed by the native enzyme isolated from Aspergillus. An "inactive" polypeptide is one which lacks the native activity, or in which the native activity has been substantially altered with respect to substrate utilization (type or amount), and/or with respect to product formation (type or amount), but which has at least the above indicated amount of homology of amino acid sequence to native GO, or to a comparable fragment of GO. Methods for detecting non-naturally occurring forms of GO and analogs of GO are known in the art. Non-naturally occurring forms of GO and analogs of GO may be detected, for example, by their changes in binding to and elution from a variety of chromatographic materials, and by their migrations through electrophoretic gels. In addition, analogs of GO may be detected, for example, by a comparison of amino acid sequences.

One type of analog of GO is a polypeptide in which one or more normally occurring cysteine residues are deleted or substituted with other amino acids; this type of polypeptide is referred to herein as a "mutein". Methods of preparing muteins are known in the art.

As used herein, the term "hyperglycosylated GO" refers to GO which contains additional carbohydrate residues relative to the amount of carbohydrate linked to native GO. The term "underglycosylated GO" refers to GO which contains less carbohydrate residues relative to the amount of carbohydrate linked to native GO. Techniques for determining whether a polypeptide contains more or less carbohydrate are known in the art, and include, for example, the variety of techniques which monitor the difference in molecular weight of a modified polypeptide (e.g., electrophoresis on polyacrylamide gels in the presence of SDS, as described by Laemmli) and migration through columns containing molecular sieve materials (e.g., Sephadex), as well as techniques which are based upon the affinity or lack of affinity between carbohydrate groups and materials which bind carbohydrates.

A "wild-type polypeptide" is one which has an identical amino acid sequence to the sequence encoded in the genome of the organism which is the source of the encoding sequence.

"Native GO" and like terms refers to GO isolated from the fungal source in which it is normally produced in nature from a naturally occurring genome.

A "non-native polypeptide" refers to a polypeptide produced in a host other than a host that naturally produces the polypeptide.

"Stringent conditions" for hybridization as used herein are conditions which will allow no more than a 1 base mismatch in the hybridization of two complementary sequences. Hybridization and wash conditions which are of varying degrees of stringency are known by those of average skill in the art, and are discussed, for example, in Maniatis et al. (1982).

As used herein, "yeast" includes ascosporogeous yeasts (Endomycetales), basidiosporogenous yeasts and yeast belonging to the Fungi imperfecti (Blastomycetes). The ascosporogeous yeasts are divided into two families, Spermophthoraceae and Saccharomycetaceae. The latter is comprised of four subfamilies, Schizosaccharomycoideae (e.g., genus Schizosaccharomyces), Nadsonioideae, Lipomycoideae and Saccharomycoideae (e.g., genera Pichia, Kluyveromyces and Saccharomyces). The basidiosporogenous yeasts include the genera Leucosporidium, Rhodosporiiium, Sporidiobolus, Filobasidium and Filobasidiella. Yeast belonging to the Fungi Imperfecti are divided into two families, Sporobolomycetaceae (e.g., genera Sporobolomyces, Bullera) and Cryptococcaceae (e.g., genus Candida). Of particular interest to the present invention are species within the genera Pichia, Kluyveromyces, Saccharomyces, Schizosaccharomyces and Candida. Of particular interest are the Saccharomyces species *S. cerevisiae, S. carlsbergensis, S. diastaticus, S. douglasii, S. kluyveri, S. norbensis and S. oviformis.* Species of particular interest in the genus Kluyveromyces include *K. lactis.* Since the classification of yeast may change in the future, for the purposes of this invention, yeast shall be defined as described in BIOLOGY AND ACTIVITIES OF YEAST (F. A. Skinner, S. M. Passmore & R. R. Davenport eds. 1980) (Soc. App. Bacteriol. Symp. Series No. 9). In addition to the foregoing, those of ordinary skill in the art are presumably familiar with the biology of yeast and the manipulation of yeast genetics. See, e.g., BIOCHEMISTRY AND GENETICS OF YEAST (M. Bacila, B. L. Horecker & A. O. M. Stoppani eds. 1978); THE YEASTS (A. H. rose & J. S. Harrison eds. 2nd ed., 1987); and THE MOLECULAR BIOLOGY OF THE YEAST SACCHAROMYCES (Strathern et al. eds. 1981).

As used herein, "fungi" includes the classes Phycomycetes, Ascomycetes, Basidiomycetes, and Deuteromycetes. Representative groups of Phycomycetes include, for example, Rhizopus, Mucor, and aquatic watermolds. Representative groups of Ascomycetes include, for example, Neurospora, Penicillium, Aspergillus, and the true yeasts, listed above. Examples of Basidiomycetes include, for example, mushrooms, rusts, and smuts.

II. Description of the Invention

The practice of the present invention will employ, unless otherwise indicated, conventional techniques of molecular biology, microbiology, recombinant DNA, and enzymology, which are within the skill of the art. Such techniques are explained fully in the literature. See e.g., Maniatis, Fitsch & Sambrook, MOLECULAR CLONING; A LABORATORY MANUAL (1982); DNA CLONING; VOLUMES I AND II (D. N. Glover ed. 1985); OLIGONUCLEOTIDE SYNTHESIS (M. J. Gait Ed., 1984); NUCLEIC ACID HYBRIDIZATION (B. D. Hames & S. J. Higgins eds. (1984); TRANSCRIPTION AND TRANSLATION (B. D. Hames & S. J. Higgins eds. 1984); ANIMAL CELL CULTURE (R. I. Freshney ed., 1986); B. Perbal, A PRACTICAL GUIDE TO MOLECULAR CLONING (1984); the treatise, METHODS IN ENZYMOLOGY (Academic Press, Inc.) and particularly Vols. 154 and 155 (Wu and Grossman, and Wu, eds., respectively); GENE TRANSFER VECTORS FOR MAMMALIAN CELLS (J. H. Miller and M. P. Calos eds., 1987, Cold Spring Harbor Laboratory); IMMUNOCHEMICAL METHODS IN CELL AND MOLECULAR BIOLOGY (Academic Press, London), and Scopes, PROTEIN PURIFICATION; PRINCIPLES AND PRACTICE, 2nd edition (Springer Verlag, 1987).

All patents, patent applications, and publications mentioned herein, both supra and infra, are hereby incorporated herein by reference.

A nucleotide construct encoding GO may be used in methods to produce the enzyme by recombinant methods.

DNA encoding GO, more specifically fungal GO, even more specifically GO from Aspergillus, and even more specifically GO from *A. niger*, was isolated from a cDNA library created by reverse transcribing poly-A+RNA isolated from *A. niger* in log-phase growth. However, the creation of probes to screen the library for sequences encoding GO was problematic. Data on both the amino acid sequence and the nucleotide sequence which encodes the fungal enzyme were lacking. Moreover, the surprising result that the attempts to sequence the enzyme isolated from *A. niger* yielded only the sequence of the first ten amino acids of the native polypeptide, necessitated devising another approach to design sequences which could be used to screen for GO-encoding sequences.

In order to design probes which would be suitable for detecting cDNA sequences encoding GO in a lambda gt10 library, oligopeptide fragments of the native enzyme from *A. niger* were purified and the amino acid sequences were determined. Based upon the sequences, oligonucleotide probes were designed in two ways. Probes of 17 to 23 nucleotides were made from the regions of lowest degeneracy. Alternatively, unique longer probes were based upon guesses of codon bias. The sequences of these probes are shown in FIG. 2.

Screening of the lambda gt10 *A. niger* cDNA library yielded surprising results. First, none of the short probes were useful for detecting clones containing GO cDNA. In addition, while two 42-mer probes could be used successfully to detect these clones, a 72-mer probe of which the 42-mer probes were subsets except for one nucleotide, was not useful for the detection. The 42-mer probes which can be used to detect GO cDNA containing clones are shown in FIG. 3.

Using the 42-mer probes, clones of lambda gt10 which contained nucleotide sequences encoding the GO polypeptide, or fragments thereof, were obtained; the cDNAs in these clones were subcloned and sequenced. A composite cDNA constructed from two of the GO cDNAs is shown in FIG. 5B. The amino acid sequence of GO was deduced from the nucleotide sequence encoding it. From the sequence it may be determined that the mature protein consists of 583 amino acids; the amino acid sequence contains only 3 cysteine residues, and 8 consensus glycosylation sites. In the amino acid sequence there is a prepro-sequence of 22 amino acids, with a single basic cleavage site at the beginning of the mature sequence.

The recombinant polynucleotide shown in FIG. 5B encodes GO from *A. niger*. It may be assumed, however, that GO from other sources, particularly other fungal sources, and more particularly from other species of Aspergillus, contain regions which are homologous to that of the GO from *A. niger*. Regions of homology can be determined by comparing the amino acid sequence of the GO from the other source with that of GO from *A. niger*; the amino acid sequence derived from the GO cDNA sequences is shown in FIG. 5B. If the amino acid sequence of the oligopeptide fragments can be compared to the sequence of *A. niger* GO. Information on the codon bias of the source may also be compared; the codon bias of *A. niger* is presented in FIG. 6. Thus, probes may be designed from the sequence in FIG. 5B which are useful in the screening of cDNA libraries or genomic libraries from other sources to detect GO encoding sequences from these sources. Parameters for designing probes are known to those of average skill in the art, and some are provided in the Examples. Usually the probes will contain at least 8 bases, more preferably at least 20 bases, and even more preferably at least 40 bases which are identical with a sequence in the cDNA sequence in FIG. 5B. The identity may be with either the coding or non-coding strand of the cDNA. These probes will hybridize under stringent conditions with the appropriate strand of the DNA duplex containing GO encoding sequence(s) to be isolated. Stringent hybridization conditions are known in the art and are discussed, for example, in Maniatis et al. (1982), and in Methods in Enzymology. The GO encoding sequences which have been detected with the probe(s) may then be cloned and isolated by utilizing techniques which are known to those of ordinary skill in the art. See, for example, Maniatis (1982), B. Perbal (1984), and Glover ed. (1985).

The isolation of a sequence encoding a portion of GO from Penicillium, more specifically *P. amagasakiense*, is described in the Examples. The isolation was accomplished utilizing a probe derived from GO cDNA contained within a recombinant vector described herein. Utilizing the fragment encoding Penicillium GO to derive probes, it is possible to derive the entire sequence of polynucleotide encoding this fungal enzyme from cDNA or genomic libraries created from the Penicillium source.

Although a method for preparing a DNA construct encoding *A. niger* GO based upon the creation of a cDNA library has been described, in the current invention the preparation of such constructs is not limited to this method. Utilizing the sequence information provided herein, other methods of preparing polynucleotide constructs encoding GO may be devised. For example, the nucleotide sequence encoding GO may be synthesized utilizing automated DNA synthesis. See, e.g. Edge (1981), Nambair et al. (1984), and Jay et al. (1984). Alternatively, oligonucleotides containing a portion of the sequence information may be synthesized; these may then be used as probes to screen genomic DNA libraries and cDNA libraries. The basic strategies for preparing oligonucleotide probes and DNA libraries, as well as their screening by nucleic acid hybridization, are well known to those of ordinary skill in the art. See, e.g., D. P. Glover ed. (1985); B. D. Hames & S. J. Higgins eds. (1985); M. J. Gate ed. (1984); Maniatis et al. (1982); and B. Perbal (1984).

Once a sequence encoding GO has been prepared or isolated, it can be cloned into any suitable replicon to create a vector, and thereby be maintained in a composition which is substantially free of vectors that do not contain the GO gene (e.g., other clones derived from the library). Numerous cloning vectors are known to those of skill in the art, and the selection of an appropriate cloning vector is a matter of choice. Examples of vectors which are suitable for cloning recombinant DNA and host cells which they can transform include the bacteriophage lambda (E. coli), pBR322 (E. coli), pACYC177 (E. coli), pKT230 (gram-negative bacteria), pGV1106 (gram-negative bacteria), pLAFR1 (gram-negative bacteria), pME 290 (non-E. coli gram-negative bacteria), pHV14 (E. coli and B. subtilis), pBD9 (Bacillus), pIJ61 (Streptomyces), YIp5 (Saccharomyces), YCp19 (Saccharomyces), and bovine papilloma virus (mammalian cells). See generally, T. Maniatis et al. (1982), B. Perbal (1984), and Glover, ed. (1985).

The polynucleotide sequence encoding GO is expressed by inserting the sequence into an appropriate replicon thereby creating an expression vector, transforming compatible host cells with the resulting expression vector, and growing the host cells under conditions which allow growth and expression.

In creating an expression vector, the GO coding sequence is located in the vector so that it is operably linked with the appropriate control sequences for expression, and possibly for secretion. At a minimum, the control sequences include a promoter, and transcriptional and translational stop codons. The positioning and orientation of the coding sequence with respect to the control sequences is such that the coding sequence is transcribed under the "control" of the control sequences: i.e., the promoter will control the transcription of the mRNA derived from the coding sequence, and the stop codon used to terminate translation will be upstream from the transcriptional termination codon.

In addition to control sequences, it may be desirable to add regulatory sequences which allow for regulation of the expression of GO relative to the growth of the host cell. This is particularly true when GO is to be expressed in cells which are grown in glucose containing media, since the hydrogen peroxide formed by GO may be toxic to the cell. Examples of regulatory systems are those which cause the expression of a gene to be turned on or off in response to a chemical or physical stimulus, including the presence of a regulatory compound. In prokaryotic systems would include the lac and trp operator systems. In yeast this could include, for example, the ADH2 system. In the Examples, the expression of GO in S. cerevisiae is under the regulatory hybrid promoter, ADH2/GAP. Other examples of regulatory sequences are those which allow for gene amplification. In eukaryotic systems, these include the dihydrofolate reductase gene which is amplified in the presence of methotrexate, and the metallothionein genes, which are amplified with heavy metals. In these cases, the sequence encoding GO would be placed in tandem with the regulatory element.

Other types of regulatory elements may also be present in the vector, i.e., those which are not necessarily in tandem with the sequence encoding GO. Enhancer sequences, for example the SV40 enhancer sequence, are of this type. An enhancer sequence by its mere presence, causes an enhancement of expression of genes distal to it.

Modification of the sequence encoding GO, prior to or subsequent to its insertion into the replicon, may be desirable or necessary, depending upon the expression system chosen. For example, in some cases it may be necessary to modify the sequence so that it will have the appropriate orientation when attached to the control sequences. In some cases, it may be desirable to add or change sequences which cause the secretion of the polypeptide from the host organism, with subsequent cleavage of the secretory signal. In the Examples, expression vectors were created which had either the natural pre-pro sequence for A. niger GO, or in which the alpha-factor from yeast was used as the secretory signal. In addition, in some cases it may be desirable to remove introns from sequences isolated from genomic libraries, to allow expression in systems, for example prokaryotic systems, which are incapable of the excision of the intron sequences, or which will not allow expression of the coding sequences containing the intron(s). An example of the latter is discussed in Innis et al. (1985). The techniques for modifying nucleotide sequences utilizing cloning are well known in the art. They include, e.g., the use of restriction enzymes, or enzymes such as Bal31 to remove excess nucleotides, and of chemically synthesized oligonucleotides for use as adapters, to replace lost nucleotides and in site directed mutagenesis. See, e.g., Maniatis et al. (1982), Glover, ed. (1985), and Hames and Higgins eds. (1984).

Modification of the sequence encoding GO may also be necessary for the synthesis of polypeptides substantially similar to GO. These polypeptides differ in some engineered way from the enzyme isolated from its native source. E.g., if a fragment of GO is the desired product, the sequence encoding the enzyme would be modified to remove the undesired sequences corresponding to the amino acids which are to be deleted. If an active fragment of GO is the desired product, the deleted sequences most likely would be in the regions of the amino- and or carboxy- terminus.

Alternatively, polypeptides substantially similar to GO may be synthesized by expressing the native gene in a host which causes a modification in the processing and/or folding of the polypeptide. In the Examples, it is shown expression of a recombinant sequence encoding A. niger GO in yeast leads to hyperglycosylated species which maintain their activity. Surprisingly, however, the yeast expressed polypeptide has greater thermostability than the native enzyme, which may increase its utility in commercial processes.

It may also be of interest to synthesize analogs of GO. Such analogs may, for example, vary in their specific activity, and or the ease with which they are expressed, and/or the ease with which they are secreted, and/or the ease with which they are purified. It is known, for example, that highly glycosylated polypeptides are often difficult to purify. The data in the Examples provide the surprising result that removal of the carbohydrate residues from GO derived from *A. niger* does not affect the enzymatic activity of the polypeptide. Thus, it may be desirable to vary, for example, the number of glycosylation sites. In addition, cys residues may be mutated to aid in the folding of recombinant and/or modified polypeptides or to alter other properties to make a protein with greater commercial utility. For example, it is shown in Section IV.I that substitution of serine for cysteine at position 521 increases the thermostability of the yeast expressed recombinant GO derived from *A. niger*.

In the examples herein, analogs of the wild-type *A. niger* GO which were recombinantly produced, and which exhibited GO enzymatic activity, are described.

It may also be of interest to synthesize analogs of fragments of GO. Such analogs which may include inactive analogs may be useful, for example, in the production of antibodies to GO.

It may also be of interest to synthesize analogs or fragments of GO which differ in their hydrophobicity, allowing greater or lesser interactions with membranes, or with liposomes. This may be accomplished by substituting hydrophobic amino acids for hydrophilic amino acids in some of the external domains of the polypeptide, or vice versa. Such changes in hydrophobicity are accomplished by modifying the sequences encoding the specific amino acids which are to be substituted.

In cases where GO is to be used in the production of foodstuffs, it may be desirable to remove immunogenic regions of the polypeptide which give rise to allergenic reactions, particularly in humans. Methods for testing for allergenicity are known to those of skill in the art.

Polypeptides which are substantially similar to GO or its fragments, but which contain an alteration in the active site, may also be synthesized. In this case the sequence encoding the enzyme would be modified so that those codons encoding the amino acids of the active site would be altered or deleted.

Polypeptides which are substantially similar to GO or its fragments include, also, polypeptides in which a portion or all of the GO sequence is fused to a sequence encoding another polypeptide. The fusion may occur at either the N-terminus or the C-terminus of the GO polypeptide or fragment. Techniques for creating fusion proteins are known in the art, and include, for example, ligating the open reading frames encoding the polypeptides so that they are in frame, and so that the expression of the fused polypeptide is under the regulation of a single promoter and terminator. Fusion may also be created by chemical means of post-expression polypeptides. Chemical methods for fusing (or linking) polypeptides are known by those of skill in the art. See, for example, Methods in Enzymology.

The above are examples of the way GO can be modified by modification of the sequence encoding GO. These examples are not meant to be exhaustive, and one skilled in the art can readily determine other modifications which would be useful. All of these modifications may be accomplished using the techniques and references cited above and below, concerning the modification of nucleotide sequences.

The sequence encoding a polypeptide substantially similar to GO, including wild-type GO, may be ligated to the control sequences to form an expression cassette prior to the insertion into the replicon which will form an expression vector. Alternatively, the coding sequence can be cloned directly into an expression vector which already contains the control sequences and an appropriate restriction site.

The control sequences in the vector will be selected so that they are compatible with the transformed host, to allow for expression and/or secretion of the molecule. These control sequences may be of mixed origins. For example, in one of the Examples described below, the expression of *A. niger* GO in *S. cerevisiae* was under the control of totally heterologous sequences, i.e., the yeast regulated yeast promoter, ADH2/GAP, the yeast alpha-factor for secretion, and the yeast GAP terminator. In another example the controls were only partially heterologous, i.e., secretion was regulated by the prepro sequence from *A. niger* (while the remainder of expression was controlled by yeast sequences. In cases where GO is expressed in prokaryotic systems, the sequence encoding the enzyme will be free of introns.

A number of replicons which may be used to construct prokaryotic expression vectors are known in the art. See, e.g., U.S. Pat. Nos. 4,440,859; 4,436,815, 4,431,740, 4,431,739, 4,428,941, 4,425,437; 4,418,149, 4,422,994, 4,366,246, and 4,342,832. Replicons which may be used to construct yeast expression vectors are also known in the art. See, e.g., U.S. Pat. Nos. 4,446,235, 4,443,539, 4,430,428, and the Examples described herein. An example of a replicon which can be used to construct an expression vector for mammalian host cells is described in commonly owned U.S. Ser. No. 921,730, the disclosure of which is incorporated herein by reference.

A preferred system for expressing recombinant GO is in yeast, preferably *S. cerevisiae*. As described in the Examples, infra, this system expresses relatively high levels of GO, particularly when the sequence encoding the wild-type *A. niger* enzyme is under the control of the yeast ADH2/GAP promoter, the yeast alpha-factor, and the yeast GAP terminator.

Depending on the expression system and host selected, a polypeptide which is substantially similar to GO, including GO, or an analog of GO, or a fragment of GO, is produced by growing host cells transformed by an expression vector described above under conditions whereby the polypeptide is expressed. The synthesized polypeptide is then isolated from the host cells and purified. If the expression system secretes the enzyme into growth media, the protein can be purified directly from the media. If the recombinant polypeptide is not secreted, it is isolated from cell lysates. The selection of the appropriate growth conditions and recovery methods are within the skill of the art.

Isolation of the newly synthesized polypeptide depends upon an assay system by which the polypeptide may be detected. These assay systems would be obvious to one skilled in the art. For example, if the newly synthesized polypeptide exhibits GO enzymatic activity, the polypeptide can be detected by assaying for the enzymatic activity. Assays for enzymatic GO activity are described below in the Examples.

It is also possible to detect the newly synthesized polypeptide by immunoassay using antibodies to polypeptides substantially similar to GO, including GO. In this case, the type of antibody used in the assay will reflect the expected presence or absence of specific known epitopes. The techniques of immunoassay are well known to those of skill in the art, and polyclonal antibodies to GO from *A. niger* are commercially available.

The expressed polypeptide may be isolated and purified to the extent needed for its intended use. Purification may be by techniques known in the art, for example, salt fractionation, chromatography on ion exchange resins, affinity chromatography, centrifugation, and the like. See, for example, METHODS IN ENZYMOLOGY and Scopes (1987) for a variety of methods for purifying proteins.

In general, recombinant production of GO can provide substantial quantities of compositions of that enzyme substantially free of contaminating proteins, i.e., of at least 90% purity. The ability to obtain substantial quantities of the polypeptide at high levels of purity is a result of recombinant expression systems which allow the recombinantly produced polypeptide to be secreted into the medium. Thus, by applying conventional techniques to recombinant cultures, GO compositions of substantial purity and amount are obtainable.

It should be noted that with the sequence data of the present invention, production of GO is not restricted to recombinant methods. It may also be synthesized by chemical methods, such as solid-phase peptide synthesis. Such methods are known to those of average skill in the art.

The recombinant polypeptides which are substantially similar to GO, including GO, can be used to produce antibodies, both polyclonal and monoclonal. If polyclonal antibodies are desired, a selected mammal (e.g., mouse, rabbit, goat, horse, tec.) is immunized with purified GO or fragment thereof, or analog thereof, or fragment of an analog thereof. Serum from the immunized animal is collected and treated according to known procedures. If serum containing polyclonal antibodies to GO contains antibodies to other antigens, the GO polyclonal antibodies can be purified by immunoaffinity.

Monoclonal antibodies to GO can also be readily produced by one skilled in the art. The general methodology for making monoclonal antibodies by hybridomas is well known. See, e.g., Schreier et al. (1980), Hammerling et al. (1981), Kennet et al. (1980). Panels of monoclonal antibodies produced against GO can be screened for various properties; i.e., for isotype, epitope, affinity, etc. Monoclonal antibodies directed against specific epitopes are useful in defining interactions of GO. In addition, monoclonal antibodies are useful in purification, using immunoaffinity techniques, of native or recombinantly produced GO.

If GO or polypeptides substantially similar to GO are to be used therapeutically, it may be desirable to link the polypeptide molecule to an efficient system to deliver the GO to the appropriate site, and which will also protect the polypeptide from proteolysis, and at the same time cause a controlled delivery of the polypeptide. Systems for the delivery of molecules are known to those of skill in the art, and are reviewed, for e.g., in Poznansky et al. (1980). Drug delivery systems may include, for example, liposomes, or antibodies directed towards specific target cells.

III. General Methods

The general techniques used in extracting polynucleotides from the source cells, preparing and probing a cDNA and/or genomic library, sequencing clones, constructing expression vectors, transforming cells, and the like, are known in the art, and laboratory manuals are available describing these techniques. However, as a general guide, the following sets forth some sources currently available for such procedures, and for materials useful in carrying them out.

III.A. Hosts and Expression control Sequences

Both prokaryotic and eukaryotic host cells may be used for expression of desired coding sequences when appropriate control sequences which are compatible with the designated host are used. Among prokaryotic hosts, *E. coli* is most frequently used. Expression control sequences for prokaryotes include promoters, optionally containing operator portions, and ribosome binding sites. Transfer vectors compatible with prokaryotic hosts are commonly derived from for example, pBR322, a plasmid containing operons conferring ampicillin and tetracycline resistance, and the various pUC vectors, which also contain sequences conferring antibiotic resistance markers. These markers may be used to obtain successful transformants by selection. Commonly used prokaryotic control sequences include the beta-lactamase (penicillinase) and lactose promoter systems (Chang et al. 1977), the tryptophan (trp) promoter system (Goeddel et al. 1980), and the lambda-derived $P_L$ promoter and N gene ribosome binding site (Shimatake et al., 1981) and the hybrid tac promoter (De Boer et al., 1983) derived from sequences of the trp and lac UV5 promoters. Sequences which when fused to a coding sequences causes the secretion of the expressed polypeptide from *E. coli* are also known, and include the bacterial pelB gene (pectate lyase) from *Erwinia carotovora* (Lei et al., 1987). The foregoing systems are particularly compatible with *E. coli*; however, if desired, other prokaryotic hosts such as strains of Bacillus or Pseudomonas may be used, with corresponding control sequences.

Eukaryotic hosts include yeast and mammalian cells in culture systems. *S. cerevisiae* and *S. carlsbergensis* are the most commonly used yeast hosts, and are convenient fungal hosts. Yeast compatible vectors carry markers which permit selection of successful transformants by conferring prototrophy to auxotrophic mutants or resistance to heavy metals on wild-type strains. Yeast compatible vectors may employ the 2 micron origin of replication (Broach et al., 1983), the combination of CEN3 and ARS1 or other means for assuring replication, such as sequences which will result in incorporation of an appropriate fragment into the host cell genome. Control sequences for yeast vectors are known in the art and include promoters for the synthesis of glycolytic enzymes (Hess et al., 1968; Holland et al., 1978), including the promoter for 3 phosphoglycerate kinase (Hitzeman, 1980). Terminators may also be included, such as those derived from the enolase gene (Holland, 1981), or from the glyceraldehyde-3 phosphate dehydrogenase (GAP) (see the Examples). Particularly useful control systems are those which comprise the GAP promoter or alcohol dehydrogenase regulatable promoter, or hybrids thereof (See the Examples), terminators derived from GAP, and if secretion is desired, leader sequences from yeast alpha-factor. In addition, the transcriptional regulatory region and the transcriptional initiation region which are operably linked may be such that they are not naturally associated in the wild-type organism. These systems are described in detail in U.S. Ser. No. 468,589, 522,909, 760,197, 868,639, 073,381, 081,302, and 139,682 filed 22 Feb. 1983, 12 Aug. 1983, 29 Jul. 1985, 29 May 1986, 13 Jul. 1987, 3 Aug. 1987, and 30 Dec. 1987, respectively, all of which are assigned to the herein assignee, and which are incorporated herein by reference.

Mammalian cell lines available as hosts for expression are known in the art and include many immortalized cell lines available from the American type Culture Collection (ATCC), including HeLa cells, Chinese hamster ovary (CHO) cells, baby hamster kidney (BHK) cells, and a number of other cell lines. Suitable promoters for mammalian cells are also known in the art and include viral promoters such as that from Simian Virus 40 (SV40), Rous sarcoma virus (RSV), adenovirus (ADV), and bovine papilloma virus (BPV). Mammalian cells may also require terminator sequences and poly A adenylation sequences; enhancer sequences which increase expression may also be included, and sequences which cause amplification of the gene may also be desirable. These sequences are known in the art. Vectors suitable for replication in mammalian cells may include viral replicons, or sequences which insure integration of the appropriate sequences into the host genome.

III.B. Transformations

Transformation may be by any known method for introducing polynucleotides into a host cell, including, for example packaging the polynucleotide in a virus and transducing a host cell with the virus, and by direct uptake of the polynucleotide. The transformation procedure used depends upon the host to be transformed. For example, transformation of *S. cerevisiae* with expression vectors encoding GO is discussed in the Example section, infra. Bacterial transformation by direct uptake generally employs treatment with calcium or rubidium chloride (Cohen (1972); Maniatis (1982)). Yeast transformation by direct uptake may be carried out using the method of Hinnen et al. (1978). Mammalian transformations by direct uptake may be conducted using the calcium phosphate precipitation method of Graham and Van der Eb (1978), or the various known modifications thereof.

III.C. Vector Construction

Vector construction employs techniques which are known in the art. Site-specific DNA cleavage is performed by treating with suitable restriction enzymes under conditions which generally are specified by the manufacturer of these commercially available enzymes. In general, about 1 microgram of plasmid or DNA sequence is cleaved by 1 unit of enzyme in about 20 microliters buffer solution by incubation of 1–2 hr at 37° C. After incubation with the restriction enzyme, protein is removed by phenol/chloroform extraction and the DNA recovered by precipitation with ethanol. The cleaved fragments may be separated using polyacrylamide or agarose gel electrophoresis techniques, according to the general procedures found in Methods in Enzymology (1980) 65:499–560.

Sticky ended cleavage fragments may be blunt ended using *E. coli* DNA polymerase I (Klenow) in the presence of the appropriate deoxynucleotide triphosphates (dNTPs) present in the mixture. Treatment with S1 nuclease may also be used, resulting in the hydrolysis of any single stranded DNA portions.

Ligations are carried out using standard buffer and temperature conditions using T4 DNA ligase and ATP; sticky end ligations require less ATP and less ligase than blunt end ligations. When vector fragments are used as part of a ligation mixture, the vector fragment is often treated with bacterial alkaline phosphatase (BAP) or calf intestinal alkaline phosphatase to remove the 5'-phosphate and thus prevent religation of the vector; alternatively, restriction enzyme digestion of unwanted fragments can be used to prevent ligation.

Ligation mixtures are transformed into suitable cloning hosts, such as *E. coli*, and successful transformants selected by, for example, antibiotic resistance, and screened for the correct construction.

III.D. Construction of Desired DNA Sequences

Synthetic oligonucleotides may be prepared using an automated oligonucleotide synthesizer as described by Warner (1984). If desired the synthetic strands may be labeled with $^{32}P$ by treatment with polynucleotide kinase in the presence of $^{32}P$-ATP, using standard conditions for the reaction.

DNA sequences, including those isolated from cDNA libraries, may be modified by known techniques, including, for example site directed mutagenesis, as described by Zoller (1982). Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. The resulting double stranded DNA is transformed into a phage supporting host bacterium. Cultures of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labeled synthetic probe at temperatures and conditions which permit hybridization with the correct strand, but not with the unmodified sequence. The sequences which have been identified by hybridization are recovered and cloned.

III.E. Hybridization with Probe

DNA libraries may be probed using the procedure of Grunstein and Hogness (1975). Briefly, in this procedure, the DNA to be probed is immobilized on nitrocellulose filters, denatured, and prehybridized with a buffer containing 0–50% formamide, 0.75M NaCl, 75 mM Na citrate, 0.02% (w/v) each of bovine serum albumin, polyvinyl pyrollidone, and Ficoll, 50 mM Na Phosphate (pH 6.5), 0.1% SDS, and 100 micrograms/ml carrier denatured DNA. The percentage of formamide in the buffer, as well as the time and temperature conditions of the prehybridization and subsequent hybridization steps depends on the stringency required. Oligomeric probes which require lower stringency conditions are generally used with low percentages of formamide, lower temperatures, and longer hybridization times. Probes containing more than 30 or 40 nucleotides such as those derived from cDNA or genomic sequences generally employ higher temperatures, e.g., about 40°–42° C., and a high percentage, e.g., 50%, formamide. Following prehybridization, 5'-$^{32}P$-labeled oligonucleotide probe is added to the buffer, and the filters are incubated in this mixture under hybridization conditions. After washing, the treated filters are subjected to autoradiography to show the location of the hybridized probe; DNA in corresponding locations on the original agar plates is used as the source of the desired DNA.

III.F. Verification of Construction and Sequencing

For routine vector constructions, ligation mixtures are transformed into *E. coli* strain HB101 or other suitable host, and successful transformants selected by antibiotic resistance or other markers. Plasmids from the transformants are then prepared according to the method of Clewell et al. (1969), usually following chloramphenicol amplification (Clewell (1972)). The DNA is isolated and analyzed, usually by restriction enzyme analysis and/or sequencing. Sequencing may be by the dideoxy method of Sanger et al. (1977) as further described by Messing et al. (1981), or by the method of Maxam et al. (1980). Problems with band compression, which are sometimes observed in GC rich regions, were overcome by use of T-deazoguanosine according to Barr et al. (1986).

IV. Examples

Described below are examples of the present invention which are provided only for illustrative purposes, and not to limit the scope of the present invention. In light of the present disclosure, numerous embodiments within the scope of the claims will be apparent to those of ordinary skill in the art. The procedures set forth, for example, in Section IV may, if desired, be repeated but need not be, as techniques are available for construction of the desired nucleotide sequences based on the information provided by the invention. Expression is exemplified in *Saccharomyces cerevisiae*; however, other systems are available as set forth more fully in Section IIIA.

All DNA manipulations were done according to standard procedures, unless otherwise indicated. See Maniatis et al. (1982). Enzymes other than glucose oxidase were utilized as per the manufacturer's specifications or the supplier's directions. Enzymes, unless indicated otherwise, were obtained from either New England Biolabs or Bethesda Research Laboratories. Yeast were transformed and grown using a variety of media, including selective medium (yeast nitrogen base without leucine); YEPD medium, containing 1% (w/v) yeast extract, 2% (w/v) peptone; and 2% (w/v) glucose, and others, as described below. In the case of plating medium, it contained 2% (w/v) agar and for transformation, 3% top agar with 1M sorbitol.

*E. coli* strains useful for transformation include Chi1776; K12 strain 294 (ATCC No. 31446); RR1, HB101 and D1210. Yeast strains useful for transformation include AB110 and GRF 180.

Yeast strain AB110 is of the genotype Mat alpha, ura3-52, leu2-04, or both leu2-3 and leu2-112, pep4-3, his4-580, cir°. A sample of this strain containing a different heterologous plasmid was deposited with the ATCC on 9 May 1984 under Accession No. 20709. See EPO Pub. No. 164,556.

Yeast strain GRF 180 is of the genotype leu2-3, leu2-112, his3-11, his3-15, CAN, cir*. This strain can be obtained by curing strain GRF18 [obtained as described in European Patent Application No. 858701070.9 (publication no. 0 184 575)] of its endogenous 2 millimicron plasmid using pC1/1 or a related plasmid as described by Erhard and Hollenberg (1983).

GO activity was measured by coupling the peroxidase-o-dianisidine system to the GO catalyzed reactions. Assays for GO which are based on this coupled system are described in the literature accompanying commercial preparations of GO supplied by Sigma Corporation, and by Worthington Corporation. Generally, the reaction is carried out in an aqueous solution in the presence of buffer at pH 5.0–6.0, beta-D-glucose, horseradish peroxidase, and o-dianisidine. The oxidation of the dye by the hydrogen peroxide generated in the reaction is monitored by the increase of optical density at 450nm or 500nm. One unit of GO activity is defined as that amount of enzyme liberating one micromole of hydrogen peroxide per minute under the specified reaction conditions.

IV.A. Preparation, Isolation and Sequencing of cDNA Encoding GO from *A. niger*

Generally, cDNA encoding GO from *A. niger* was obtained by screening a cDNA library constructed in lambda gt10 with oligonucleotide probes which were developed based upon the amino acid sequences of peptide fragments of purified GO.

IV.A.1. Preparation of a cDNA Library which contains GO encoding sequences from *A. niger*

In order to define a source of nucleic acids encoding GO, strains of *A. niger* obtained from the American Type Culture Collection were screened for GO production. One strain in particular, *A. niger* 9029, was used as a source of mRNAs from which the cDNA library could be prepared since it was determined that this strain produced and secreted GO into the medium. In order to determine whether GO was produced, the strain was grown in YEPD medium, and GO activity in the conditioned media was determined. GO activity was measured by coupling the peroxidase-o-dianisidine system to the GO system.

The presence of GO in the conditioned medium was confirmed by Western blot analysis using a preparation of rabbit anti-GO antibody, which was obtained from Accurate Chemicals.

The cDNA library was prepared from poly A+RNA which was isolated from mycelia of *A. niger* 9029, which were in log-phase growth in YEPD medium. First, total RNA was isolated by a modification of the procedure of Chirgwin et al. (1979). This method involves breaking cells in 4M guanidium thiocyanate and 0.1M mercaptoethanol to denature proteins and break disulfide bonds. The RNA is then separated from DNA and proteins by ultracentrifugation through a 5.7M CsCl cushion as described by Glisin (1974), except that a vertical rotor (VTi50, Beckman) as opposed to a swinging bucket rotor is used. The poly A+RNA fraction was isolated as described by Maniatis et al. (1982), using two passages over oligodT cellulose. The synthesis of cDNA from the poly A+RNA, and the creation of a cDNA library from the *A. niger* 9029 poly A+RNA in lambda gt10 were carried out according to a method described by Huynh (1985); cDNA synthesis was by reverse-transcriptase using random primers. The complexity of the library was $1.6 \times 10^6$.

IV.A.2. Preparation of Probes and Screening of Library

In order to design probes which would be suitable to screen the lambda gt10 library for phage containing cDNA encoding GO (GO cDNA), the amino acid sequence of oligopeptide fragments of purified GO were determined. This program was followed since, surprisingly, attempts to obtain the amino acid sequence of the entire polypeptide were unsuccessful, and yielded a sequence for only the first ten amino acids.

Commercially obtained GO was further purified by electrophoresis on a polyacrylamide gel in the presence of sodium dodecylsulfate (SDS) under the conditions described by Laemmli (1970). The protein was eluted from the gel, and was fragmented by digestion with trypsin or with cyanogen bromide (CNBr), which procedures are standard methods in protein chemistry. CNBr digests were in 70% formic acid. Trypsin digests were performed after treatment of the GO with citraconic anhydride which specifically blocks lysine residues, reducing the specificity of trypsin to the unmodified arginine residues. The protein was typically reduced and carboxymethylated using mercaptoethanol and iodoacetic acid prior to these treatments to break any disulfide bonds present.

The resulting peptides were separated and purified by HPLC. A number of methods were used. Both neutral and acidic reverse-phase systems using acetonitrile gradients were employed. Initially, fragments were separated into size classes using Bio-Gel P-10 in 30% formic acid, or separated into charge classes using ion exchange chromatography in 6M urea buffer systems; FPLC Mono-S and Mono-Q columns were used to further separate fragments for sequence analysis. In order to ensure that the peptide fragment to be analyzed was pure, the purification on HPLC was typically run twice; i.e., the purified fragment was subjected to further purification by repeating the HPLC procedure. The amino acid sequences of the peptide fragments of GO were determined using a gas-phase sequenator (Applied Biosystems), according to the manufacturer's directions. The sequences of the fragments which resulted from this analysis are shown in FIG. 1. In the figure, the parentheses indicate uncertainties in the sequence as read from chromatograms, with the exception of the Arg or Met residues at the N-termini which are assumed from the specificity of the cleavage reagent (trypsin or CNBr).

Oligonucleotide probes were designed in two ways. Probes of 17 to 23 nucleotides were made from regions of lowest degeneracy. Alternatively, unique longer probes were based upon guesses of codon bias. Probes which were designed to screen the lambda gt10 library containing sequences encoding GO from *A. niger* are shown in FIG. 2. The figure shows the amino acid sequence of the fragments, and the probes derived from the sequences. Also shown is the size of the oligomeric probe, and for the shorter probes, the degree of degeneracy.

The lambda gt10 library was screened for GO cDNA containing clones using the above-designed probes. The probes were prepared by chemical synthesis according to conventional procedures using phosphoramidite chemistry as described in Urdea et al. (1983). The synthetic probes were labeled with $^{32}P$ using $T_4$ polynucleotide kinase in the presence of $^{32}P$-ATP. The method for labeling probes is described in Maniatis et al. (1982).

The screening of the lambda gt10 library with the probes was essentially as described by Huynh (1985). Filters were hybridized overnight at room temperature with 100,000 dpm/ml of each of probes long 6, long 7, and long 8 in 4×SSC, 50 mM Na Phosphate, pH 6.8, 2×Denhardt's solution, and 0.3 mg/ml sonicated salmon sperm DNA. They were then washed at 47° C. in 3.0M tetramethylammonium chloride according to Wood et al. (1985), and autoradiographed for 6 days. None of the short probes were useful for detecting clones containing GO cDNA. The library was also screened with probes long 6, long 7, and long 8 as a pool; after 6 days of exposure, 4 light double-positives were obtained from the $4 \times 10^5$ phage which were screened. Upon repeat screening with the pool, these four clones remained positive for GO cDNA. The phage were then replated in triplicate, and screened with the three individual long probes. The four clones hybridized with probes long 7 and long 8. However, none of the clones hybridized with long 6. This result was surprising since, with the exception of a single base change, probes long 7 and long 8 are subsets of long 6. (See FIG. 3).

The presence in the four positive clones of cDNA which binds the long 7 and long 8 probes was confirmed by Southern blot analysis of the DNAs. DNA which was isolated from each clone was treated with EcoRI, and analyzed by Southern blot analysis as described by Maniatis et al. (1982), using a mixture of probes long 7 and long 8. In each clone, only a single band hybridized with the probes. The sizes of the cDNAs in the bands were 0.9 kB, 0.9 kB, 0.3 kB, and 0.7 kB for clones 1–4, respectively.

Evidence that the cDNA in clone 4 overlapped that in the three other clones was obtained by showing that the cDNA insert isolated from clone 4 hybridized with the cDNA inserts of clones 1, 2, and 3 under conditions of high stringency. The cDNA insert from clone 4 was excised with EcoRI, isolated by gel electrophoresis, and $^{32}P$-labeled by nick translation. The method for nick translation was as described by Maniatis (1982). The other three clones were digested with EcoRI, electrophoresed on a 1% agarose gel and blotted onto nitrocellulose. The nick translated clone 4 probe was denatured and hybridized to the Southern blot under the conditions described above for screening the cDNA library except that the mix contained 50% formamide and the incubation was done at 42° C. overnight. The filter was then washed at 60° C. in 0.1×SSC and autoradiographed.

IV.A.3. Nucleotide Sequence of GO cDNA

The cDNAs in clones 1–4 were determined by the method of Sanger et al. (1977). Essentially, the cDNA was excised from the clones with EcoRI, and isolated by size fractionation using gel electrophoresis. The EcoRI restriction fragments were subcloned into the M13 vectors, mp18 and mp19 [Messing (1983)], and sequenced using the dideoxy chain termination method of Sanger et al. (1977).

The nucleotide sequence of the EcoRI fragment (approximately 700 bp) from clone 4 is shown in FIG. 4. The restriction enzyme map of the fragment is shown in FIG. 4A. The nucleotide sequence, as well as the amino acids encoded therein, is shown in FIG. 4B. The positions of the restriction enzyme sites are also indicated in FIG. 4B. The GO cDNA fragment in clone 4 consists of a single open reading frame. Two of the peptide fragments which were analyzed by amino acid sequence analysis are encoded in the clone 4 GO cDNA, except that two of the 36 amino acid residues are altered. The amino acid sequences of the fragments are shown in FIG. 1.

A composite cDNA can be constructed from the nucleotide sequences of the GO cDNAs in clones 1 and 2, the latter of which is probably a full length cDNA clone. The nucleotide sequence of the composite cDNA is shown in FIG. 5. FIG. 5A shows a restriction enzyme map of the sequence. FIG. 5B shows the composite nucleotide sequence derived from the clones, and indicates the restriction enzyme sites. Also shown in FIG. 5B are the amino acids encoded in the sequence. From the sequences it can be determined that the mature protein consists of 583 amino acids; the amino acid sequence contains only 3 cysteine residues, and 8 consensus glycosylation sites. In the amino acid sequence there is a prepro-sequence of 22 amino acids, with a single basic cleavage site (Arg-Ser) at the beginning of the mature sequence.

Evidence that the composite cDNA sequence encodes GO was obtained by a comparison of the amino acid sequences of the peptide fragments from purified GO (See Section IV.A.2) with those encoded in the composite cDNA. This comparison is shown in FIG. 6, in which the derived amino acid sequence is indicated over the nucleotide sequence. Those amino acid sequences which correspond to sequences in the peptide fragments from purified GO are underlined. Disparities in the derived sequence and the sequence in the fragments from purified GO are also indicated. It may be seen from FIG. 6 that there are very few differences between the cDNA derived sequences and those of the isolated GO peptides.

FIG. 6 also presents data on the molecular weight of the polypeptide which includes the signal peptide, and on the codon usage in *A. niger*, based upon the nucleotide sequence encoding GO.

It may be predicted from the composite cDNA sequence that the mature unglycosylated GO would have a molecular weight of 63,300. The mature polypeptide contains 8 consensus glycosylation sites. Assuming 2 kD of carbohydrate for each site, the MW of a glycosylated GO monomer would be 79 kD. This is consistent with the observed molecular weight of a GO monomer, which is 75 kD. Moreover, the amino acid composition derived from the cDNA sequence is in agreement with the amino acid composition reported in the literature. The reported amino acid composition has been confirmed in separate experiments (not shown). In addition, as shown infra in Section IV, expression of the cDNA yields active glucose oxidase.

IV.B. Isolation and Sequence Analysis of Genomic Sequences Encoding GO

The oligonucleotide probes described above in Section IV.A.2, and nick-translated fragments of the GO cDNAs, which were isolated as described in Section IV.A.2, were used in the isolation of a genomic *A. niger* clone from a pBR322 based *A. niger* library made in *E. coli* strain DH5.

IV.B.1. Construction of the *A. niger* library and Isolation of Genomic Clones Encoding GO.

Genomic DNA was prepared from *A. niger* 9029 cells by the method of Boel et al. (1984). The DNA (50 micrograms) was treated with Sau3a under conditions which yield partial digestion (1 unit of Sau3a in 1 ml volume for 50 minutes at 37° C.), and the reaction was quenched by the addition of EDTA. The digested DNA was run on a preparative 1% agarose gel and DNA in the size range 7-10 kB was isolated. This DNA was ligated into pBR322 which had been linearized with BamHI, treated with alkaline phosphatase, and gel isolated. The resulting ligated DNA was transformed into *E. coli* and plated onto 10 large plates. A total of 340,000 transformants were obtained. Plasmid DNA was prepared from each plate separately, yielding approximately 35,000 recombinants. 60,000 colonies from a single pool were plated and duplicate nitrocellulose replicas made. A 600 bp NcoI-EcoRI fragment from cDNA clone 2 was nick translated and used as a probe under the conditions described supra. After autoradiography 4 potential clones were obtained, one of which, 17a, was later shown to be correct by Southern blotting and sequence analysis.

IV.B.2. Restriction Fragment Length Analysis of the Genomic DNA Encoding GO

The presence or absence of introns in genomic sequences may be determined by comparing the sizes of fragments of cDNA and genomic DNA obtained by restriction enzyme digestion. The fragments are analyzed by the Southern method, using a probe to detect sequences which encode GO.

Genomic clone 17a and the cDNA clone pBRlambda2A were both digested with NcoI, which cuts 4 times in the cDNA yielding a particular pattern of small fragments. After analysis on both agarose and acrylamide gels, the NcoI restriction pattern was shown to be the same for both clones. Subsequently, clone 17a DNA was digested with EcoRI, XhoI, SalI, and HindIII; the digestion was alone, and in combinations of pairs. These digests were electrophoresed on agarose gels and transferred to nitrocellulose filters. The filters were probed with a 600 bp NcoI-EcoRI fragment from the 5'-half of the cDNA and with an 1100 bp EcoRI fragment from the 3'-half of the genomic sequence in clone 17a. These probes had been labeled with $^{32}P$ by nick translation. In all cases, the genomic map was congruent with the cDNA map.

In addition, genomic DNA from *A. niger* was digested with the same enzymes, blotted, and hybridized with the same probes. The results yielded the same pattern as that seen with clone 17a. These results indicate that rearrangements and/or deletions had not occurred during the cloning procedure.

The analysis by Southern blotting indicated that the restriction enzyme fragments detected by the probes were the same sizes in the GO cDNAs, in the genomic clones, and in the genomic sequences in DNA isolated from *A. niger*. This provides evidence for the surprising result that the *A. niger* genomic DNA encoding GO lacks intron sequences.

IV.B.3.Nucleotide Sequence of the GO promoter region

It is presumed that the region which flanks the 5'-terminus of the sequence encoding GO contains the promoter sequences for the gene. This region and the contiguous region which encodes the NH$_2$-region of GO were isolated as a polynucleotide fragment from a genomic clone of GO, and the nucleotide sequence of the isolated fragment was determined.

The promoter region of the GO gene was isolated from the genomic clone 17a (see Section IV.B.4. for the preparation of genomic clones). The fragment was cleaved from the pBR322 vector sequences by digestion with EcoRI and SalI, and the fragment of approximately 609 bp was isolated by gel electrophoresis. The isolated fragment was cloned into M13 vectors, and sequenced by the dideoxy chain termination method (See Section IV.A.3.). The sequence of this region is shown in FIG. 7. The restriction enzyme map of the sequence is shown in FIG. 7A; the sequence, and the restriction enzyme sites are shown in FIG. 7B. Also shown in FIG. 7B is the amino acid sequence of the NH₂-terminal region of GO, which is encoded in the genomic clone.

IV.C. Construction of Vectors for the Expression of GOcDNA in Yeast

Two expression vectors for the production of GO in yeast were constructed. In these expression vectors, the sequences encoding GO are operably linked to sequences for transcription and expression of the GO polypeptide. Both vectors contain the ADH2-GAP hybrid promoter for regulated transcription. In addition, to cause secretion, either the *S. cerevisiae* alpha-factor leader sequence or the GO prepro sequence is fused to the mature GO coding sequence.

Figure 8:
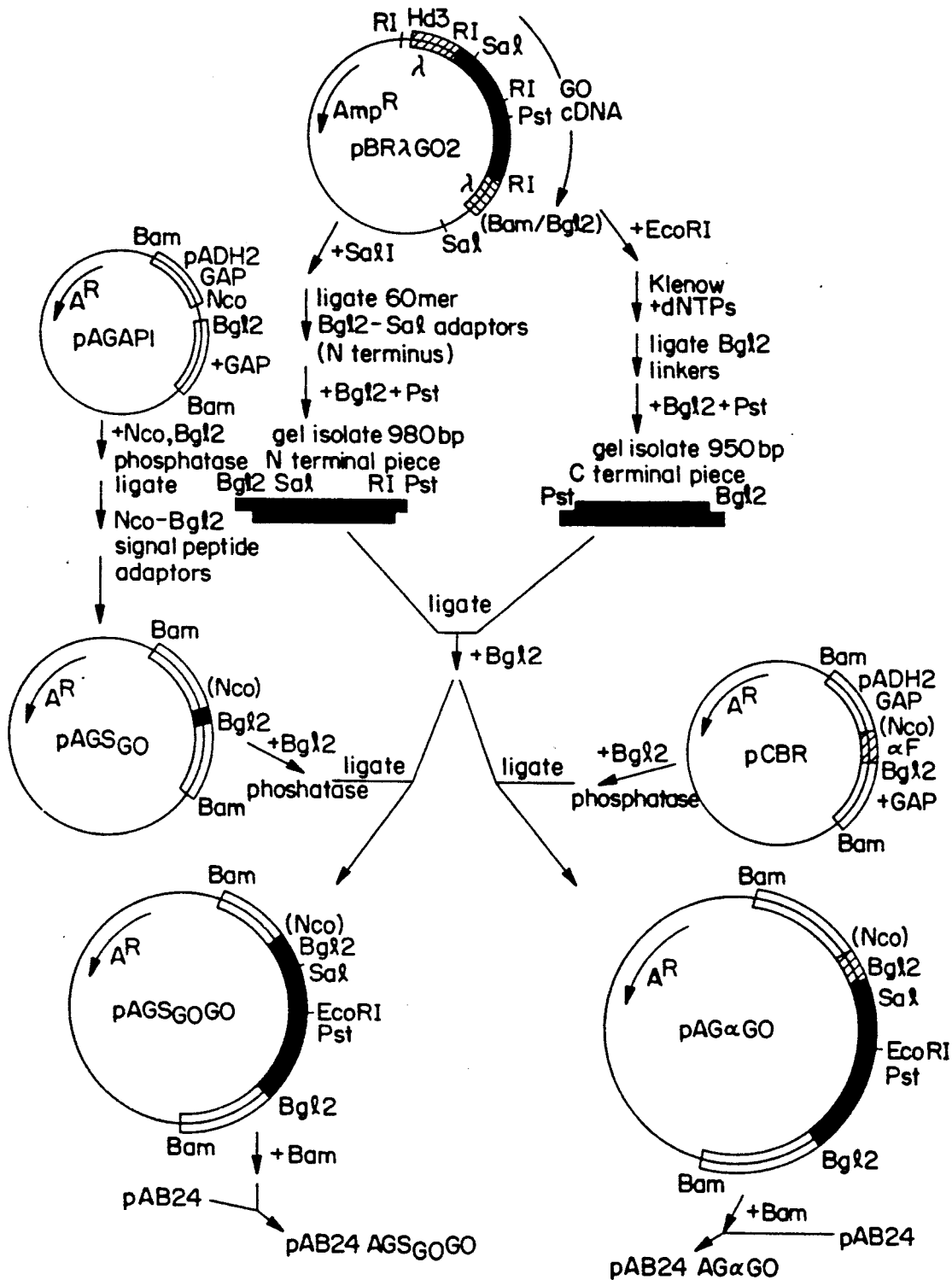
FIG. 8 shows a flow chart for the construction of expression vectors pAB24AGS$_{GO}$GO and pAB24AG$_{al\text{-}pha}$GO.

The GO cDNA from clone 2 (see Section IV.A.2.) was excised from lambda gt10 as an HindIII-BglII fragment. The resulting restriction fragment, which contained some flanking lambda gt10 DNA, was inserted between the HindIII and BamHI sites of pBR322, to create the vector pBRlambda-GO2. The schemes for the construction of the expression vectors utilizing the GO cDNA sequences in pBRlambda-GO2 are shown in FIG. 8.

IV.C.1. Construction of an Expression Cassette in pAGS$_{GO}$GO

An expression cassette contained in a plasmid which replicates in *E. coli*, in which the sequences encoding GO were operably linked to control sequences, which included the yeast ADH2-GAP hybrid promoter, the GAP terminator, and the secretory signal which was derived from the *A. niger* GO gene, was constructed as follows.

pBRlambda-2a DNA was digested with SalI, which cuts approximately 120 bp from the N-terminus of the GO coding sequence, and which cuts once in pBR322. A synthetic duplex encoding the N-terminus of the mature GO coding sequence was prepared and ligated to this digest. The sequence of the duplex was:

```
5' AGATCTAATGGCATTGAAGCTTCCCTCCTGACTGATCCCAAGGATGTCT
     ATTACCGTAACTTCGAAGGGAGGACTGACTAGGGTTCCTACAGA

CCGGCCGCACGG     3'
GGCCGGCGTGCCAGCT
```

BglII site was conveniently placed at the N-terminus of mature GO, by silent mutations in the sequence encoding Arg-Ser. After ligation, the mixture was digested

5' GAGATCTC 3'

The resulting fragment was digested with BglII and PstI. After this treatment, the GO cDNA fragment, which was 950 bp, was isolated by gel electrophoresis.

The 980 bp fragment and the 950 bp fragment were ligated. Since ligation could occur at the sticky ends derived from both PstI and BglII, the ligated fragments were treated with BglII, thus yielding GO cDNA which contained sticky ends which could form BglII sites.

The vector pAGAP1 is a derivative of pPGAP1 in which the alcohol dehydrogenase - glyceraldehyde-3 phosphate dehydrogenase (ADH2-GAP) regulatable promoter is substituted for the glyceraldehyde-3 phosphate dehydrogenase (GAPDH) promoter. The plasmid pPGAP1 is described in Travis et al. (1985), in EPO Publication No. 164,556, and also in commonly owned U.S. Ser. No. 760,197, filed 29 Jul. 1985; these references are incorporated herein by reference. In pAGAP1 the ADH2-GAP promoter is linked to the GAP terminator. The promoter is a 1200 bp BamHI-NcoI fragment isolated from pJS103. The construction of this promoter is described in U.S. Ser. No. 139,632, filed 30 Dec. 1987, which is assigned to the herein assignee, and which is incorporated herein by reference. The GAP terminator is a 900 bp BglII-BamHI fragment derived from pPGAP1. See EPO Publication No. 164,556. The fragment linking the promoter and terminator is:

```
       (NcoI)                          (BglII, former SalI site)
5'  CCATGGGAATTCGTTAGGTCGAGATCTCGAC  3'
    GGTACCCTTAAGCAATCCAGCTCTAGAGCTG
```

The restriction enzyme sites encoded in the sequence are indicated in the parentheses. This fragment may be replaced by genes of interest.

In order to insert the signal sequence for GO, pAGAP1 was digested with NcoI and BglII, treated with phosphatase, and ligated with the following synthetic duplex which encodes the GO prepro-sequence:

```
       (NcoI)              (XhoI)
5'  CATGCAGACTCTCCTTGTCTCGAGCCTTGTGGTCTCCCTCGC
          GTCTGAGAGGAACAGAGCTCGGAACACCAGAGGGAGCG (BglII)
    TGCGGCCCTGCCACACTACATCA  3'
    ACGCCGGGACGGTGTGATGTAGTCTAG
``` with BglII and PstI, and a 980 bp fragment containing the N-terminal half of the GO cDNA was isolated by gel electrophoresis.

The fragment which contains the C-terminal region of GO cDNA was isolated by excising the cDNA with EcoRI, treating the excised fragment with Klenow and the four deoxynucleotide triphosphates, and ligating a synthetic BglII linker to the fragment. The linker had the sequence:

The XhoI site was incorporated using silent mutations to aid in screening. The resultant plasmid, pAGS$_{GO}$, contained a BglII site downstream of the prepro sequence, into which the GO cDNA sequence could be inserted.

The insertion of the GO cDNA fragment into pAGS$_{GO}$ was accomplished by digesting the plasmid with BglII and phosphatase, and then ligating the GO cDNA to the linearized plasmid. The resulting plasmid was named pAGS$_{GO}$GO.

IV.C.2. Construction of an Expression Cassette in pAG$_{alpha}$GO

The construction of an expression cassette contained in a plasmid which replicates in E. coli, in which the sequences encoding GO were operably linked to control sequences, which included the yeast ADH2-GAP hybrid promoter and the yeast alpha-factor as a secretory signal, was similar to that for the construction of pAG$_{GO}$GO (Section IV.C.1.), except for the following.

The plasmid into which the GO cDNA fragment was ligated was pCBR, which is similar to pAGAP1, except that the alpha-factor leader has been inserted between the promoter and terminator, with a unique BglII site at the dibasic processing site (lys-arg, or in one letter code K-R), for KEX2. The plasmid which resulted from the insertion of the GO cDNA fragment into pCBR is called pAG$_{alpha}$GO.

IV.C.3. Construction of Yeast Expression Vectors Encoding GO

Yeast expression vectors in which the GO sequence is operably linked to sequences which control the expression and secretion of the GO polypeptide were constructed by excising with BamHI the expression cassettes from pAGS$_{GO}$GO and pAG$_{alpha}$GO, and inserting the expression cassettes into the unique BamHI site of the plasmid pAB24.

Figure 9:
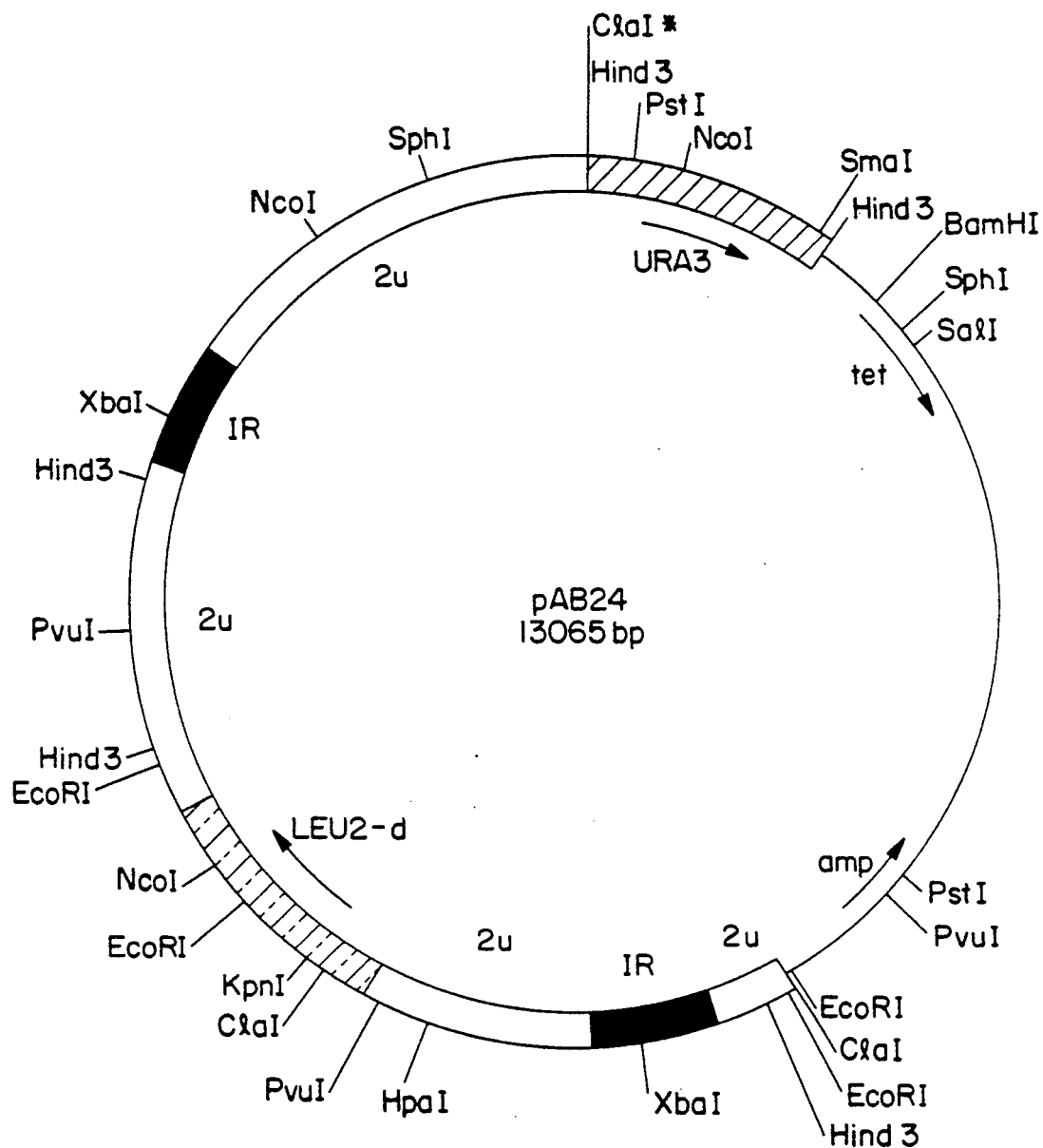
FIG. 9 is a map of the significant features of the shuttle vector pAB24.

Plasmid pAB24 (FIG. 9) is a yeast shuttle vector which contains the complete 2 micron sequence [Broach (1981)] and pBR322 sequences. It also contains the yeast URA 3 gene derived from plasmid YEp24 [Botstein et al. (1979)] and the yeast LEU2d gene derived from plasmid pC1/1. EPO Publication No. 116,201. Plasmid pAB24 was constructed by digesting YEp24 with EcoRI and religating the vector to remove the partial 2 micron sequences. The resulting plasmid, YEp24$_{delta}$Ri, was linearized by digestion with ClaI and ligated with the complete 2 micron plasmid which had been linearized with ClaI. The resulting plasmid, pCBou, was then digested with XbaI and the 8605 bp vector fragment was gel isolated. This isolated XbaI fragment was ligated with a 4460 bp XbaI fragment containing the LEU2d gene isolated from pC1/1; the orientation of the LEU2d gene is in the same direction as the URA3 gene.

In order to construct the yeast expression vectors, the expression cassettes were excised from pAGS$_{GO}$GO and pAG$_{alpha}$GO by digestion with BamHI, and plasmid pAB24 was linearized with the same restriction enzyme and digested with phosphatase. The excised expression cassettes were isolated by gel electrophoresis. The linearized plasmid was ligated with either the expression cassette from pAGS$_{GO}$GO to yield the vector pAB24AGS$_{GO}$GO, or with the expression cassette from pAG$_{alpha}$GO to yield the vector pAB24AG$_{alpha}$GO.

IV.D. Expression of GO in Yeast from pAB24AGS$_{GO}$GO-10 and from pAB24AG$_{alpha}$GO-1

Clones of two of the expression vectors for the production of GO were isolated, i.e. pAB24AGS$_{GO}$GO-10 and pAB24AG$_{alpha}$GO-1. The vectors were constructed as described in Section IV.C. Both vectors contain the ADH2-GAP hybrid promoter for regulated transcription, and either the S. cerevisiae alpha-factor leader (pAB24AG$_{alpha}$GO), or the GO prepro-sequence fused to the mature GO coding sequence (pAB24AGS-$_{GO}$GO). However, subsequent analysis of the nucleotide sequences of the sequences encoding GO revealed the presence of mutant sequences in these clones.

IV.D.1. Expression from pAB24AGS$_{GO}$GO-10 and from pAB24AG$_{alpha}$GO-1

Yeast strain GRF 180 was transformed with the indicated clones of these plasmids by the method of Hinnen (1978) and leucine prototrophs were selected. The transformants were inoculated into leucine selective media containing 8% glucose for 48 hours. The inocula were diluted to an initial A$_{650}$=0.05 into expression medium of YEP containing 2% glucose. The cultures were grown at 30° C. at 300 rpm; aliquots were harvested every 24 hours. Cells were separated from the conditioned medium by centrifugation in a microfuge for 1 min at 14,000 rpm, and glucose oxidase activity present in the media and in the cell extracts was determined, using glucose oxidase obtained from Sigma as a standard. The cell extracts were prepared by vortexing the cells with glass beads. I.e., the cell pellets were mixed with an equal volume of acid washed glass beads in lysis buffer containing 10 mM Tris pH 8, and vortexed for 5×1 minute with 1 minute on ice between vortexings. The insoluble cell debris was removed by centrifugation at 14,000 rpm in a microfuge at 4° C. The results on active glucose oxidase expressed after 72 hours of growth are shown in Table 1. In the table, the symbol "nd" means that the activity was not determined.

TABLE 1

| Expression of GO in S. Cerevisiae Strain GRF180 | | | | |
|---|---|---|---|---|
| Plasmid | pAB24 | pAB24AGS$_{GO}$GO-10 | | pAB24AGalphaGO-10 | |
| Transformant | 1 | 1 | 2 | 1 | 2 |
| | GO Activity (micrograms/ml culture) | | | | |
| Cond. Medium | 0 | 54 | 63 | 51 | 31 |
| Cell Extract | 0 | 50 | nd | 53 | nd |

The results in Table 1 indicate that GO encoded in the expression vectors is expressed in yeast, and that high levels of GO activity (>25 micrograms/ml) are secreted into the medium. No detectable activity was found from the control transformants, transformed with pAB24. Despite the high level of secreted GO activity, only about 50% of the total GO activity is secreted, suggesting that the total synthesis of GO in these transformants is very high, i.e., in some cases is >100 micrograms/ml. Moreover, surprisingly, relative to the yeast alpha-factor, the secretory signal from A. niger seems to be an efficient control sequence for the secretion of the polypeptide in S. cerevisiae.

Using a similar procedure, the expression of GO was compared when the vectors were used to transform GRF180 and AB110. The results of this comparison indicated that Strain GRF180 is preferable to Strain AB110 for both total expression and GO secretion.

IV.D 2. Characterization of the Expressed Polypeptides

IV.D.2.a. The Detection of Mutations in the Expressed Polypeptides

The detection of mutations in the polypeptides expressed in Section IV.D.1. was accomplished by DNA sequence analysis of the N-termini of the GO genes in the expression cassettes. The fragments which were sequenced were excised by digesting the vectors with SalI and SacI, and the resulting 750 bp or 940 bp pieces derived from pAB24AGS$_{GO}$GO-10 and pAB24AG$_{al\text{-}pha}$GO-1 respectively, were isolated by gel electrophoresis. The resulting fragments were cloned into M13mp18 and subjected to dideoxy sequencing. The sequences were translated into the amino acids encoded therein, and these were compared to the comparable sequences encoded in the cDNA. The results of the analysis are presented in Table 2, where the amino acid sequences are denoted in the standard one letter code.

TABLE 2

Sequence of the N-termini of GO in Several Expression Plasmids

| | |
|---|---|
| cDNA: | RSNGIEASLLTDPKDVSGR |
| pAB24AGS$_{GO}$GO-1: | RSNGIE<u>D</u>SLL<u>ID</u>P<u>E</u>DVSGR |
| pAB24AG$_{alpha}$GO-10: | RS<u>R</u>GI<u>K</u>ASLLTDP<u>K</u>RVSGR |

In Table 2, the first S residue is the first amino terminal residue of the mature polypeptide. The amino acid sequences which differ from that encoded in the cDNA are underlined. It is probable that these mutations result from impurities in the oligonucleotide linkers which were used during the construction of the expression cassettes.

IV.D.2.b. Analysis of the Expressed GO Polypeptides by Electrophoresis on Polyacrylamide Gels in the Presence of SDS: the Effect of Endoglycosidase H on Molecular Size Preliminary analysis of the media samples from IV.D.1 suggested that with both the GO and alpha-factor secretory signals, the GO which was produced was hyperglycosylated. This was further examined by analyzing the effect of endoglycosidase H (EndoH) on the molecular size of the expressed polypeptides. EndoH was obtained from Boehringer-Mannheim, and used according to the supplier's directions. This enzyme catalyzes the deglycosylation of glycosylated polypeptides.

Expression of GO was in transformants of GRF180 containing the expression vectors, pAB24AGS$_{GO}$GO-10 and pAB24AG$_{alpha}$GO-1, as described in Section IV.D.1. After 72 hours of growth in YEP medium containing 2% glucose, the media were collected. Aliquots of approximately 1 ml of each media were concentrated 10–20 fold by centrifugation using a Centricon-10 membrane. The proteins in the concentrated media were precipitated by the addition of one-half volume of 50% TCA containing 2% deoxycholate as carrier (TCA/DOC). The protein pellets were redissolved in 50 microliters of water, and one half of each sample was treated with EndoH (1–2 mUnits). The other half of each sample was incubated under the same conditions, but in the absence of EndoH. As a reference, authentic glucose oxidase from A. niger was treated in the same manner. After a second TCA/DOC precipitation to concentrate the samples, the polypeptides were run on an 8% polyacrylamide gel containing SDS under the conditions described by Laemmli (1970), and the polypeptides on the gel were visualized by staining with Coomassie blue.

From the gels it was determined that GO expressed in yeast is hyperglycosylated, since in the absence of EndoH treatment the polypeptides migrated less than did the standard GO. However, after treatment with EndoH, the yeast products migrated as a doublet of apparent molecular weight of 68–70 kD; the same doublet was observed with the EndoH treated standard GO.

In the absence of EndoH treatment, the polypeptide expressed and secreted from the vector containing the yeast alpha-factor leader has an apparent MW of 90–120 kD. The material expressed from this vector is of lower MW and appears to be less heterogenous than the GO polypeptide secreted from yeast using the GO secretion sequence. This is true despite the fact that there are 3 additional N-linked glycosylation sites in the alpha-factor leader sequence. Thus, secretion under the control of the alpha-factor leader may be more efficient. In addition, little if any material of apparent MW consistent with that of the alpha-factor leader fused to GO is observed after treatment with EndoH; this suggests that the processing by KEX2 of this fusion protein is very efficient.

It should be noted that the finding that the prepro sequence of GO functions as a secretory signal in *S. cerevisiae* is a surprising result.

IV.E. The Effect of EndoH on the Activity of GO

In order to determine the effect of the extent of glycosylation on the activity of GO, the enzyme which had been expressed in and secreted from yeast, as well as the enzyme obtained from *A. niger* was digested with EndoH. The effect of the removal of glycosyl groups on the enzymatic activity of GO was assessed.

The secreted GO polypeptides expressed in yeast were obtained and the conditioned media containing the polypeptides were concentrated as described in Section IV.D. After concentration each sample was divided into 3 aliquots. One aliquot was used to determine initial GO activity. The remaining two aliquots were incubated at 37° C. overnight in 150 microliters of solution containing 0.2M sodium citrate, pH 6, 0.12% SDS, and 1 mM phenylmethanesulfonylfluoride (PMSF). One aliquot was incubated with EndoH, and the other was incubated without EndoH. After the incubation, GO activity was determined in each of the three aliquots. In addition, portions of the aliquots were precipitated with TCA/DOC and analyzed by electrophoresis on 8% polyacrylamide gels in the presence of SDS.

The results (not shown) were the following. 1) The GO activity in the polypeptides secreted from recombinant yeast, as well as that from *A. niger* is stable for 37° C. for 20 hrs in dilute SDS. 2) Treatment with EndoH did not inactivate any of the GO activity, which was within 20% of that of the untreated samples. 3) The GO secreted from yeast under the control of its own prepro sequence is much more heavily glycosylated than that secreted under the control of the alpha-factor sequence. The apparent MW of the former is in the range of 100–200 kD, while that of the latter is in the range of 75–150 kD. 4) No change was seen in the activity of any of the samples (i.e., from the samples expressed in yeast, or from the standard GO from *A. niger*) after treatment with EndoH. Since the end-product after EndoH treatment is essentially the same molecule as far as carbohydrate content for GOs, it may be concluded that the hyperglycosylation of the product expressed in yeast has no effect on enzyme activity.

The result that GO activity was relatively independent of the extent of glycosylation of the GO polypeptide, was surprising. It has been reported for other proteins (e.g., tissue plasminogen activator), that hyperglycosylation of the polypeptide expressed in yeast substantially reduces biological activity. V. MacKay, "Secretion of Heterologous Proteins in Yeast", in BIOLOGICAL RESEARCH ON INDUSTRIAL YEASTS, Vol. II, pp 27-36, (CRC Press, Boca Raton, Fla.).

IV.F. Construction of Yeast Expression Vectors Encoding Wild-Type GO, and Expression of the Wild-Type Enzyme In order to construct wild-type glucose oxidase expression vectors, SalI-BglII 1.9 kb fragments from the mutant plasmids were isolated and were ligated with newly synthesized oligomers encoding the correct N-terminal sequence. The sequences of the oligomers were those shown supra for the construction of expression cassettes. The fragments were digested with BglII, and the corrected gene was inserted into the expression vectors. DNA sequence analysis of the inserts showed that the resulting vectors contained the correct sequences at the N-termini.

Figure 11:
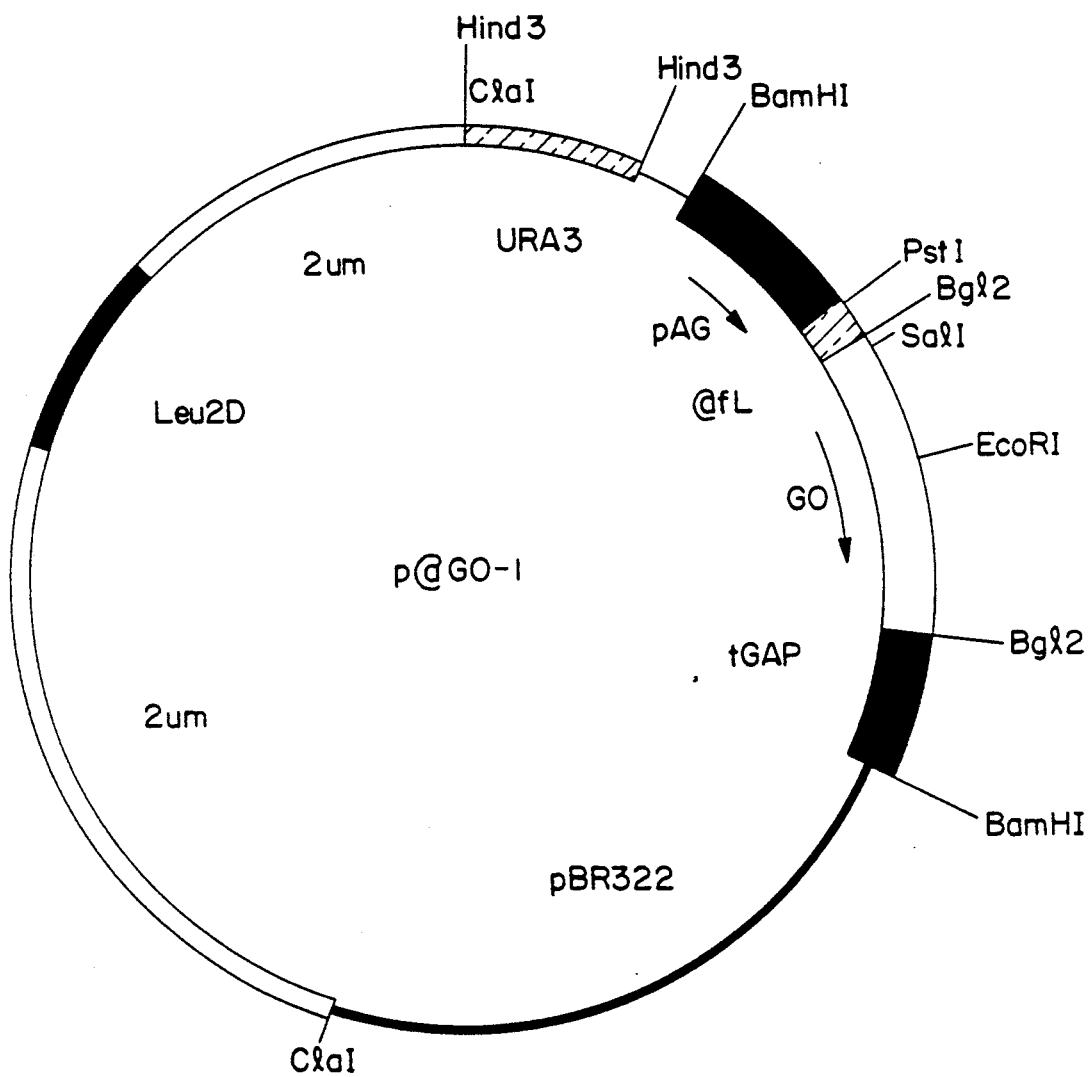
FIG. 11 is a map of p@GO-1 showing some significant features, including restriction enzyme sites.
Figure 12:
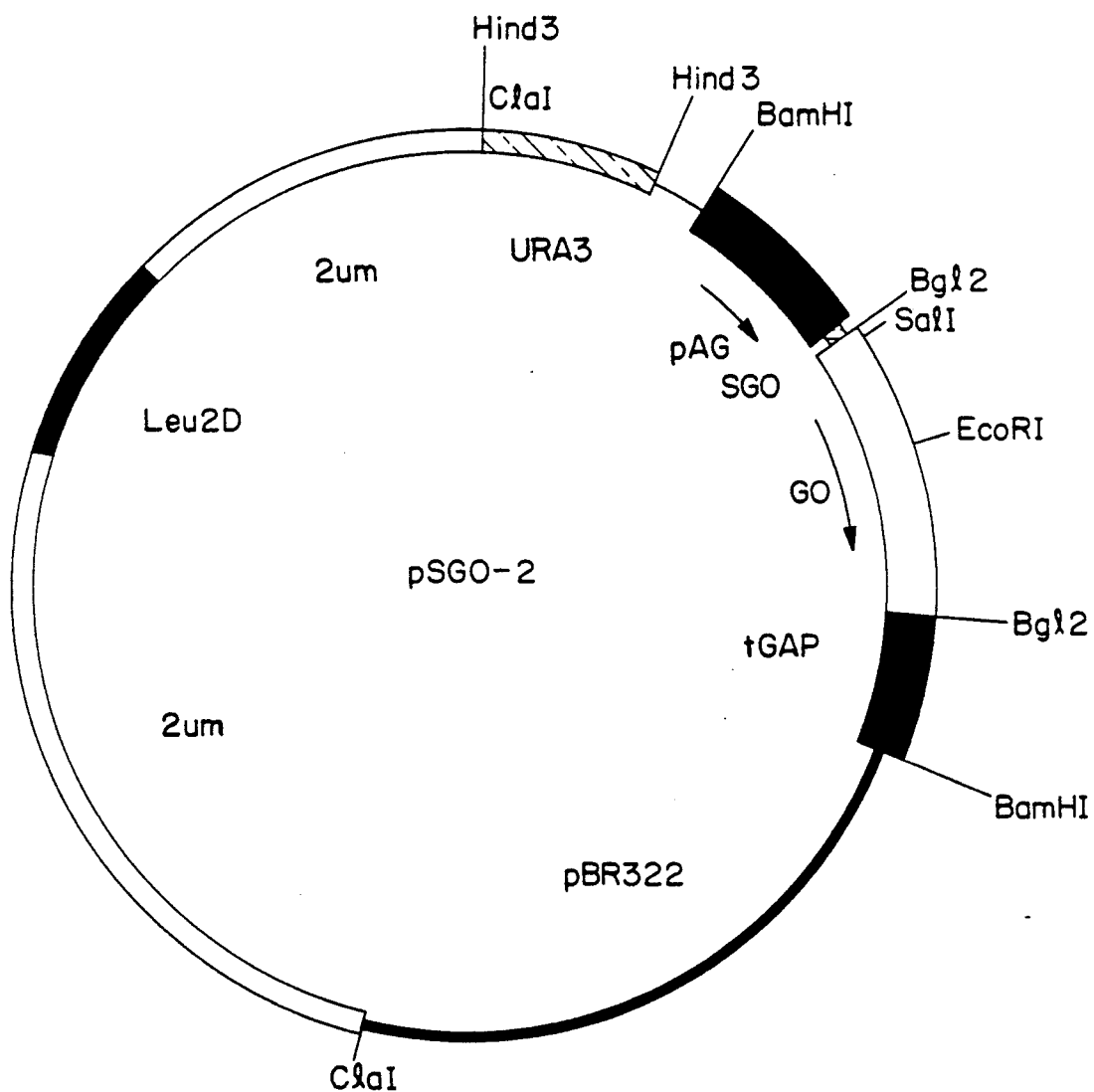
FIG. 12 is a map of pSGO-2 showing some significant features, including restriction enzyme sites.

Clones of each of these vectors have been isolated, and are named pAB24AGSGO and pAB24AG@GO for the vectors containing as secretion control elements the A. niger prepro sequence and the alpha-factor sequence, respectively. The vector pAB24AGSGO is also called pSGO2 (or pSGO-2); the vector pAB2-4AG@GO (pAB24AGalphaGO) is also called p@GO-1 (p-alpha-GO1). Restriction enzyme maps of p@GO-1 and of pSGO-2 are shown in FIGS. 11 and 12, respectively.

IV.G. Expression of Wild-type GO in Yeast and Characterization of the Expressed Polypeptides

IV.G.1 Expression of GO in Transformants of S. cerevisiae

The amount of GO activity expressed in S. cerevisiae transformed with expression vectors containing sequences encoding wild-type GO was determined.

Strain GRF180 was transformed with either of the cloned yeast expression vectors pAB24AGSGO or pAB24AG@GO. Transformation was by the method of Hinnen (1970), and leucine prototrophs were selected. Inoculation cultures of the individual transformants were made by growing the transformants in 2 ml of leucine selective media containing 8% glucose for 48 hours. Subsequently, the inocula were diluted to $A_{650}=0.05$ with non-selective media, and were grown for 96 hours at 30° C. at 300 rpm. After growth, the cells were removed from the conditioned media by centrifugation in a microfuge for 1 min at 14,000 rpm, and GO activity present in the media was determined.

The results of the glucose oxidase activity expressed in yeast from the two expression vectors, and secreted into the conditioned media, are presented in Table 3. In the table, GO activity is expressed in micrograms/ml of culture.

TABLE 3

| Expression of Wild-Type Glucose Oxidase in Transformants of GRF180 Containing Yeast Expression Vectors pAB24AGSGO or pAB24AG@GO | | | | | |
|---|---|---|---|---|---|
| Plasmid | pAB24 | pAB24AGSGO | | pAB24AG@GO | |
| Transformant | 1 | 1 | 2 | 1 | 2 |
| GO Activity | 0 | 148 | 179 | 202 | 170 |

A comparison of the results shown in Table 3 with those in Table 1 suggest that either the wild-type GO expressed in yeast has a higher specific activity than do the mutant GOs, or that the enzyme is expressed at higher levels than are the mutants.

IV.G.2. Characterization of the Expressed Polypeptides by Electrophoresis on SDS Polyacrylamide Gels: The Effect of EndoH Cultures of yeast transformants containing the expression vectors pAB24AGSGO and pAB24AG@GO were grown as described in Section IV.G.1. After growth, the cells were removed by centrifugation, and GO activity in the conditioned media was determined. Media from transformants containing pAB24AGSGO and pAB24AG@GO had GO activities of 190 micrograms/ml and 260 micrograms/ml, respectively.

Prior to digestion with EndoH, the GO polypeptides were partially purified. The media were diluted 10-fold with 0.01M acetate, pH 4.5, and passaged through DEAE-cellulose Fast Flow (Pharmacia) columns. After loading, the columns were washed with the same buffer, and then GO was eluted with 0.1M acetate, pH 3.7.

Figure 10:
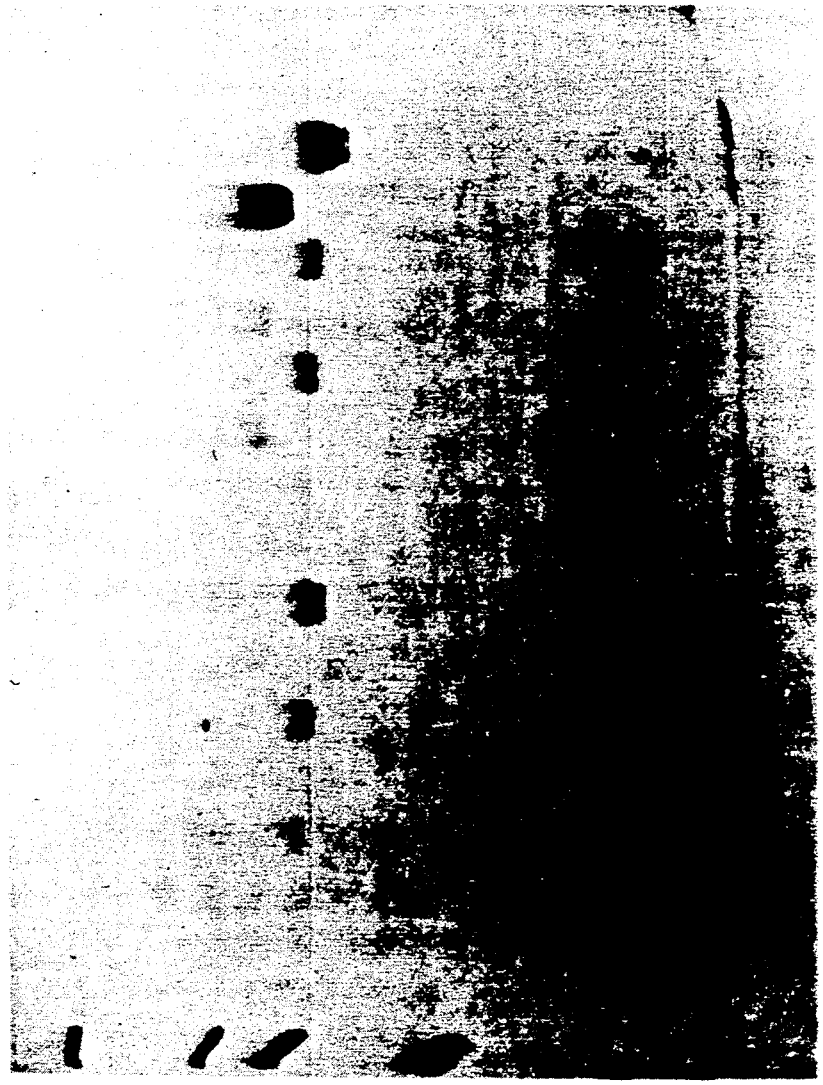
FIG. 10 shows a polyacrylamide gel on which partially purified recombinant GO was electrophoresed, when the GO had been treated in the presence and absence of endoglycosidase H.

The GO polypeptides expressed from yeast, both before and after partial purification, were digested with EndoH overnight at 37° C. The digestion conditions were as described in Section IV.E., except that 50 microliter aliquots of the samples were digested; control samples were incubated under the digestion conditions in the absence of EndoH. After the incubation, the samples were precipitated with TCA, washed 3 times with acetone to remove TCA, and the equivalent of 12.5 microliters of the original volume of each sample was loaded onto an 8% polyacrylamide gel. Electrophoresis through the gel was in the presence of SDS under reducing conditions, as described in Laemmli (1970). The polypeptides in the gel were detected by staining with Coomassie blue. A photograph of the gel is shown in FIG. 10; the samples in the various lanes are as described in Table 4, which also shows the amount of GO in the sample. In the table, the + symbol means that the sample was treated with EndoH; the − symbol means the sample was incubated under the digestion conditions in the absence of EndoH. The number in parentheses after the sample indicates the fraction number as eluted from the DEAE-cellulose column. As a control, GO from A. niger was subjected to incubation under the digestion conditions in the presence or absence of EndoH.

TABLE 4

The Effect of EndoH Digestion on the Migration of Wild-Type GO Expressed in Yeast

| Lane | GO derived from | EndoH | Amt. GO (micrograms) |
|---|---|---|---|
| M | Markers | | |
| 1 | A. niger | − | 0.2 |
| 2 | A. niger | + | 0.2 |
| 3 | pAB24AGSGO (media) | − | 2.4 |
| 4 | pAB24AGSGO (media) | + | 2.4 |
| 5 | pAB24AGSGO (fr.2) | − | 3.7 |
| 6 | pAB24AGSGO (fr.2) | + | 3.7 |
| 7 | pAB24AGSGO (fr.3) | − | 8.1 |
| 8 | pAB24AGSGO (fr.3) | + | 8.1 |
| 9 | pAB24AGSGO (fr.4) | − | 1.4 |
| 10 | pAB24AGSGO (fr.4) | + | 1.4 |
| 11 | pAB24AG@GO (media) | − | 3.2 |
| 12 | pAB24AG@GO (media) | + | 3.2 |
| 13 | pAB24AG@GO (fr.2) | − | 2.5 |
| 14 | pAB24AG@GO (fr.2) | + | 2.5 |
| 15 | pAB24AG@GO (fr.3) | − | 18.8 |
| 16 | pAB24AG@GO (fr.3) | + | 18.8 |

The results shown in the gel in FIG. 10 confirm that large amounts of GO protein are being made. Since the equivalent of only 12 microliters of yeast media were loaded in lanes 4 and 12, and >>0.2 micrograms of enzyme as compared to the standard is in the gel, the activity results are correct, and more than 200 mg/liter of GO is secreted and expressed in the yeast systems.

IV.G.3. Thermostability of the Polypeptide Expressed from pAB24AGSGO compared to native GO from *A. niger*

The thermostabilities of the purified recombinant GO polypeptide expressed in yeast from pAB24AGSGO and that of native GO purified from *A. niger* were compared by thermal denaturation studies.

The recombinant polypeptide expressed from pAB24AGSGO as described in Section IV.G.1., was purified by a modification of the method of Pazur and Kleppe (1964). Yeast cells were removed by centrifugation and the conditioned YEP medium was diluted 10 fold with 0.01M sodium acetate, pH 4.5. This material was applied to a DEAE Sepharose Fast Flow column (20 ml) (Pharmacia) equilibrated with the same buffer. The column was then washed with 3 volumes of the equilibration buffer and the enzyme eluted with 0.1M sodium acetate (pH 3.7). Fractions containing GO activity were pooled and concentrated by ultrafiltration. Native GO purified from *A. niger* was obtained from Sigma Corp. (Type 5). Both recombinant GO and native GO were incubated at a concentration of 0.1 mg/ml in 0.1M citrate-phosphate buffer, pH 5.5, using essentially the conditions described in Malikkides and Weiland (1982). Enzyme samples were incubated at 65° C., aliquots removed at various times, and were diluted 10-fold into phosphate buffer, pH 5.5. Enzyme activity in the diluted samples was then determined using essentially the method of Kelley and Reddy (1986), with the following modifications. The assays were performed in a volume of 1.0 ml in 0.1M sodium phosphate buffer, pH 7.0, containing 0.2 mM o-dianisidine (Sigma Corp.), 10 micrograms of horseradish peroxidase (Boehringer-Mannheim Corp.), and 9.5 mM D-glucose. The assays were initiated by the addition of GO (1–30 ng), incubated at room temperature for 20 minutes, and then quenched by the addition of 0.1 ml 4N $H_2SO_4$. The resulting reduced o-dianisidine was then measured at 400 nm on a Shimazu Model UV-160 spectrophotometer or at 405 nm on an ELISA reader (Titertek Multiscan). Enzyme amounts were calculated as ng GO relative to a standard curve of absorbance versus enzyme amount. The results of the thermostability studies are shown in FIG. 13, where the percent of enzyme activity remaining is plotted against time of incubation at the elevated temperature (closed square, GO expressed in yeast; closed diamond, native GO).

Figure 13:
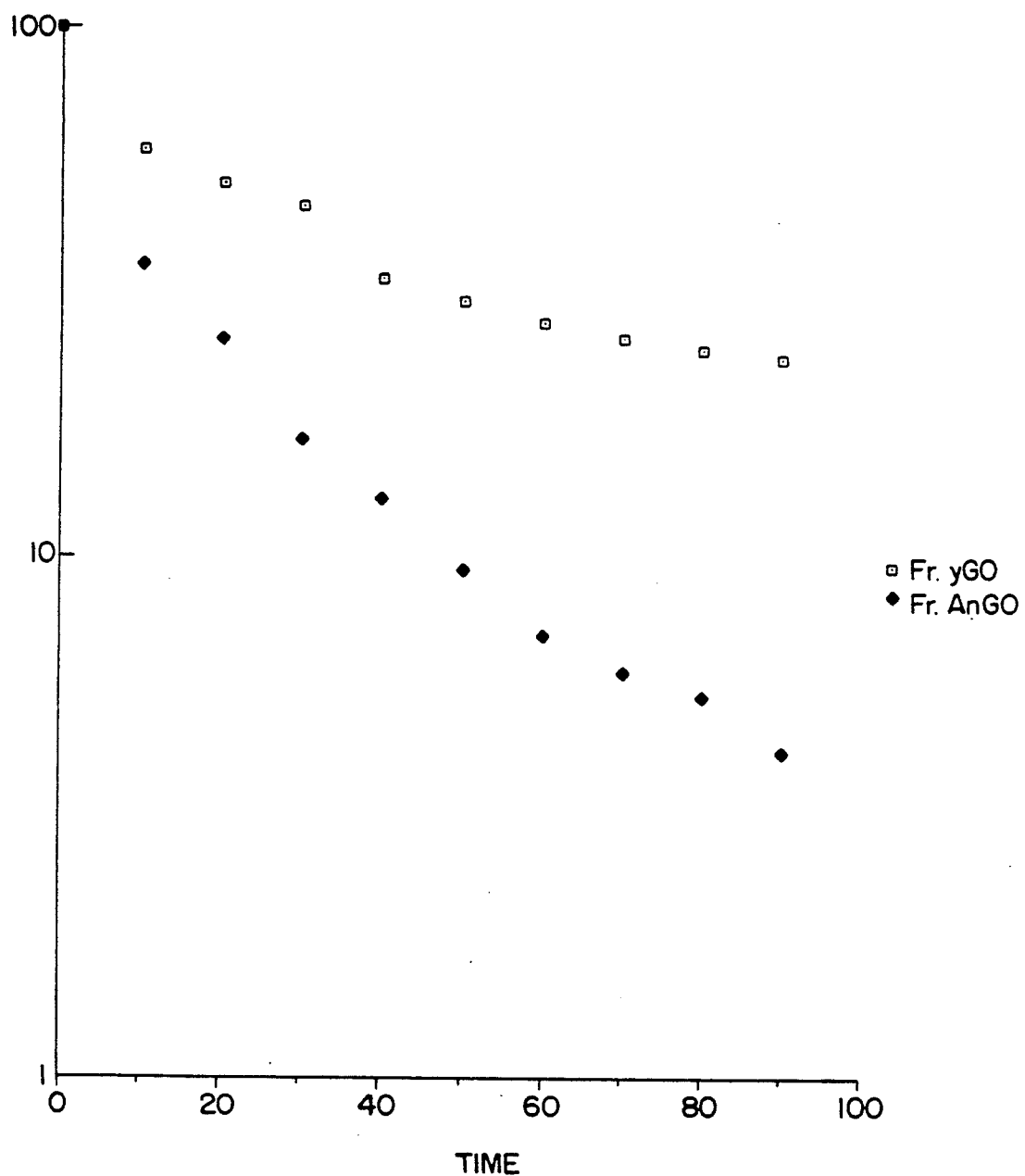
FIG. 13 is a graph showing the thermostabilities with time of the GO polypeptide expressed in yeast from pAB24AGSGO compared to native GO from *A. niger.*

The data in FIG. 13 show that a pseudo-first order rate constant of 0.04 $min_{-1}$ is obtained for the decay of the native enzyme activity, whereas the enzyme expressed in yeast has a rate constant of 0.012 $min^{-1}$. Thus, the enzyme expressed in yeast, which is hyperglycosylated, is substantially more thermostable than the native enzyme from *A. niger*.

IV.H. Assessment of GO mRNA Level

*A. niger* produce significant quantities of GO. The studies described above show that significantly more than 1 mg/L is expressed and secreted at relatively low cell densities. In addition, the protein has been detected in crude lysates of *A. niger* by Western blotting, suggesting that the enzyme represents >0.1% of the total cell protein. Thus, it would be expected that relatively large amounts of the mRNA for this enzyme would be present in *A. niger* during the log and/or stationary phases of growth. In order to assess the whether or not these mRNAs were detectable, cDNA from clones 1, 2, and 4 (described in Section IV.A.2 and Section IV.A.3) were used as probes for Northern blots of RNA isolated during log-phase growth.

Northern blotting of the RNA was performed as follows, essentially as described by Maniatis et al. (1982). Poly A+RNA (5 micrograms) isolated from *A. niger* which were in log phase of growth, was denatured with glyoxal and electrophoresed on a 1% agarose gel. The RNA was transferred to a nitrocellulose filter, and was probed with the nick-translated 1.1 kb EcoRI fragment of cDNA, using the conditions described supra for Southern blotting. After hybridization with the probe, the filters were washed at 60° C. in 1×SSC. After autoradiography for 1 week, no bands were detected. Control experiments indicated that the RNA was intact, and had efficiently transferred from the gel to the filter.

The results suggest that mRNAs encoding GO are very rare in cells of *A. niger* in log-phase growth. This result is surprising since such large amounts of GO protein are synthesized. It may explain the difficulty in obtaining the nucleotide sequence encoding GO from a cDNA library.

IV.I. Analogs of Glucose Oxidase Which are Muteins

IV.I.1. Construction of vectors Encoding Muteins

Mutated sequences encoding glucose oxidase in which each of the three cysteine codons at positions 164, 206, and 521 were substituted with serines were prepared using site directed mutagenesis using essentially Eckstein's method, as described in Taylor et al. (1985).

First, a derivative of pAB24AGSGO in which the GO 3' untranslated sequence was deleted, was prepared. In order to accomplish this, the 3'-half of the GO gene from cDNA clone 4 (described in FIG. 4) was subcloned into M13mp19 as a PstI-EcoRI fragment. Two contiguous primers were used to introduce a total of 7 mutations at the 3'-end of the GO gene. The contiguous primer sequences were the following (with the mutations underlined, the restriction enzyme sites indicated above the primer sequence, and the amino acids encoded therein in parentheses below the primer sequence):

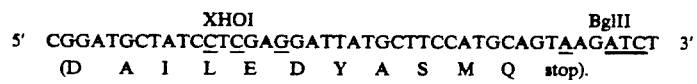

```
                  XHOI                              BglII
5' CGGATGCTATCCTCGAGGATTATGCTTCCATGCAGTAAGATCT 3'
    (I    A  I  L  E  D  Y  A  S  M  Q  stop).
```

The resulting PstI-BglII fragment encompassing the 3'-half of the GO cDNA was ligated with a BglII-PstI fragment from pAB24AGSGO comprising the 5'-half of the gene, and these were ligated into the same plasmid which had been treated with BglII and phosphatased. The resulting plasmid is pSGO3.

The mutations in which the Ser codons were substituted for the Cys codons were made using the following primers:

GOC164S: 5'
        ATTAACACCATGGCTCGAGGCATT-
        GAAGTA 3'

GOC206S: 5'
        GGGGTCACCGGATCCGAAATCTTT 3'

GOC521S: 5'
        CGGCATCATGGAACTAGTACCCACGCC
        3'.

The 5'-half of the expression cassette from plasmid pAB24AGSGO was subcloned into M13mp19 as an AhaIII-PstI fragment. The first two primers (GOC164S AND GOC206S) were used with this template; the GOC521S primer was used on the template, described above, which was used for the generation of pSGO3. After cloning, the primers were subsequently used as probes to isolate plaques containing the mutated sequences; the entire inserts of positive plaques were sequenced to verify that only the desired mutations were obtained. The mutant genes were then reconstructed into expression vectors analogous to pSGO3, except that these vectors contained the sequences of nucleotide with defined mutation. The vectors containing mutations at Cys164, Cys206, and Cys521 are named pSGO3C164S (also called C164S), pSGO3C206S (also called C206S), and pSGO3C521S (also called C521S), respectively.

IV.I.2. Expression of GO Mutein Encoding Expression Vectors in Yeast

Expression of the GO muteins encoded in pSGO3C164S, pSGO3C206S, and pSGO3C521S, and of the wild-type gene in pSGO3, was in transformants of yeast strain GRF180. Transformation and expression were essentially as described in section IV.D., except that the above listed vectors were used. The effect on expression and/or secretion and/or activity of the mutations changing the native cysteine residues at positions 164, 206, and 521 to serines are shown in Table 5.

TABLE 5

| Secreted GO Activity of Mutein Encoding Vectors | |
|---|---|
| Expression Vector | Secreted GO Activity (micrograms/ml) |
| pSGO3 | 300 |
| pSGO3C164S | <10 |
| pSGO3C206S | <10 |
| pSGO3C521S | 100 |

As seen from the results, secreted GO activity from the expression of pSGO3C164S and pSGO3C206S was undetectable. The level of secreted GO activity resulting from expression of pSGO3C521S was somewhat reduced relative to that of expression of pSGO3. From these results it is concluded that Cys164 and Cys206 are required for the expression/secretion and/or activity of GO.

IV.I.3. Thermostability of the Mutein Encoded in C521S

Figure 14:
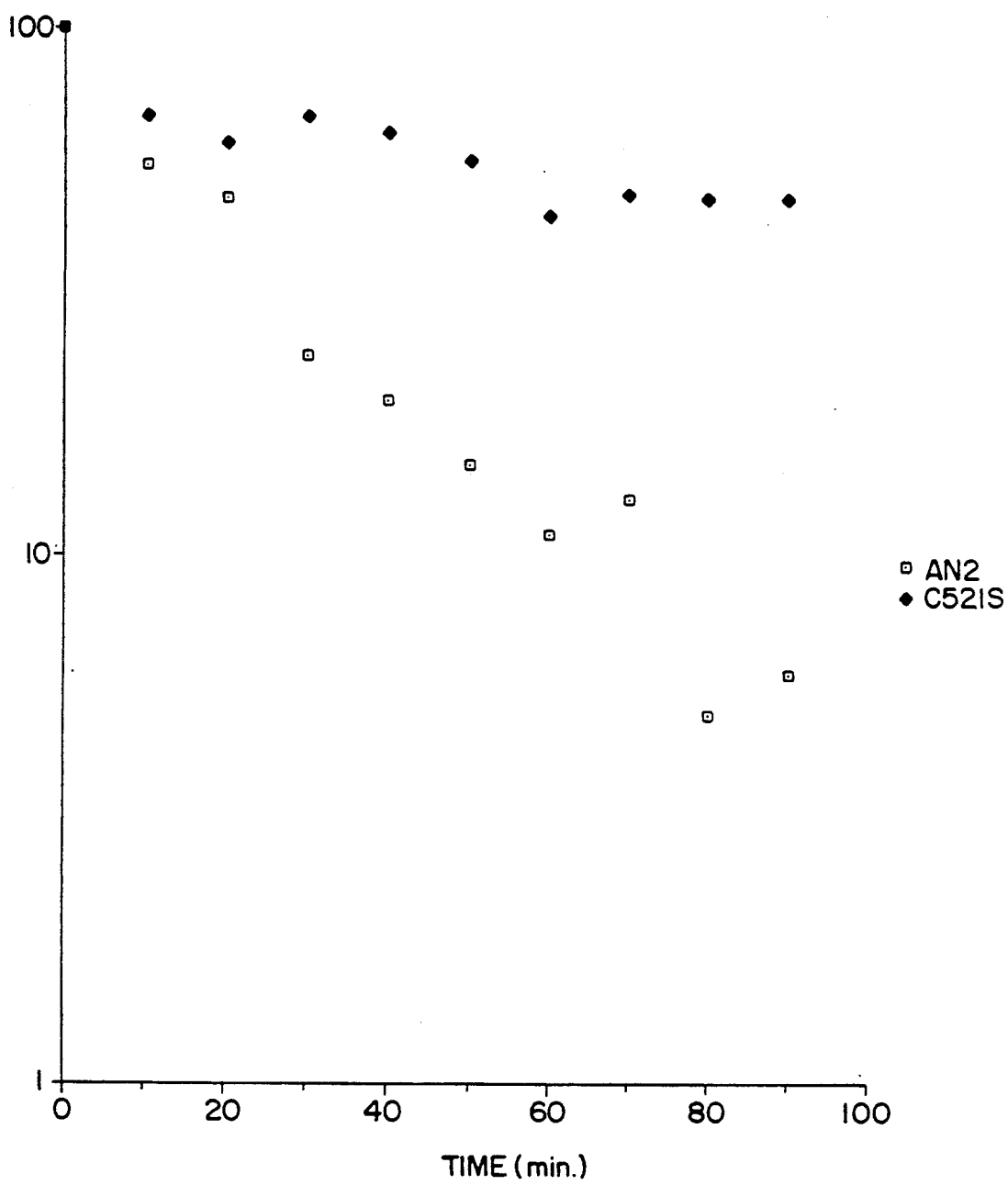
FIG. 14 is a graph showing the thermostabilities with time of the mutein encoded in C521S and expressed in yeast, compared to native GO from. *A. niger.*

The thermostability of the polypeptide expressed from pSGO3C521S transformed yeast was compared to that of native GO from *A. niger*. The thermostability studies were carried out essentially as described in Section IV.G.3. The results, plotted as percent of activity remaining after incubation at the elevated temperature versus time are shown in FIG. 14 (native enzyme, squares; pSGO3C521S encoded polypeptide, diamonds). Based upon the results, an estimate of the rate constant for inactivation is less than 0.01 min$^{-1}$. A comparison of the thermostabilities of this mutein with native GO from *A. niger* as well as that of the polypeptide encoded in pAB24AGSGO suggests that the pSGO3C521S mutein is the most thermostable of the three GO enzymes.

IV.J. Isolation of Genomic DNA Encoding GO from Penicillium

Genomic DNA encoding GO was obtained from *P. amagasakiense* as follows. *P. amagasakiense* (obtained from the American Type Culture Collection) was grown in YEP medium, and the DNA prepared essentially as described in Boel et al. (1984). The isolated DNA was digested with a variety of restriction enzymes, i.e., EcoRI, HindIII, BamHI, SalI, PstI, and XhoI, and was blotted to nitrocellulose. The blot was probed with a random prime labeled 1.9 kB BglII fragment of the *A. niger* GO gene present in plasmid pAB24AGSGO. Hybridization was with a mixture containing the probe in 20% formamide and 10% dextran sulfate, at 42° C. overnight. The filter was then washed at 50° C. with a solution of 1×SSC, 0.1% sodium dodecyl sulfate (SDS), and autoradiographed overnight. The autoradiographs showed a single specific band in each lane, suggesting that a single gene with homology to the *A. niger* GO gene was present in the *P. amagasakiense* genome. In particular, a BamHI fragment and an HindIII fragment of 2.4 kB and 1.9 kB, respectively, were seen.

Figure 15:
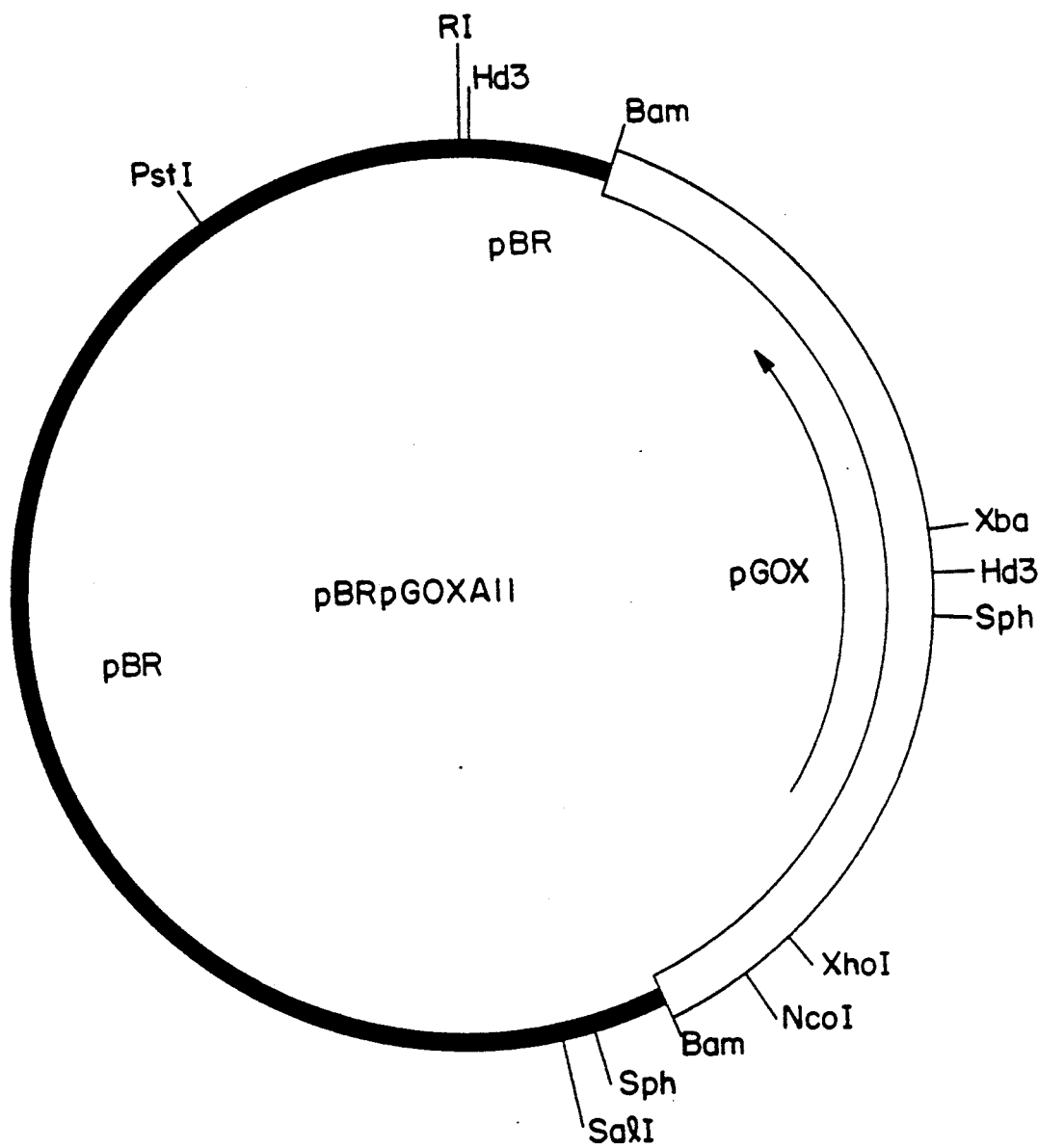
FIG. 15 is a map of restriction enzyme sites in clone pBRpGOXA11.

In order to clone the BamHI fragment, 20 micrograms of Penicillium DNA was digested with the restriction enzyme, and fragments which electrophoresed in the range of size between 2.3 and 2.6 kB were isolated from the gel. The DNA in this preparation was ligated into pBR322, which had been treated with BamHI and phosphatased. Transformation of an aliquot of the ligated plasmid DNA into *E. coli* HB101 yielded approximately 10$^4$ ampicillin resistant colonies, of which 85% were predicted to be recombinant because of their test phenotype. The potentially recombinant colonies were transferred in duplicate to nitrocellulose filters and hybridized with the above described GO probe from pAB24ASGO. Hybridization was at 37° C. with 10% formamide and 10% dextran sulfate. The filters were washed at 50° C. in a solution of 1×SSC, 0.1% SDS, and autoradiographed for 3 days. Six potential positive clones were identified, picked, and their plasmid DNAs prepared. Five of these clones contained BamHI inserts of 2.3–2.6 kB, and subsequent Southern blot analysis showed three of them to be the same. A representative plasmid, a restriction enzyme map of which is shown in FIG. 15, was named pBRpGOXA11.

Sequencing of the BamHI insert in pBRpGOXA11 was accomplished as follows. Isolated plasmid DNA was digested with BamHI, fragments of approximately 2.5 kB isolated, and further digested with HindIII. The mixture of fragments was then ligated into M13, and the DNA from potential recombinant plaques subjected to sequence analysis. The resulting sequence from one such clone, pBRA11, is shown in FIG. 16, where it may be seen that an open reading frame (ORF) is apparent throughout the entire 445 bp fragment.

A comparison of the amino acids encoded in the 445 bp fragment derived from the *P. amagasakiense* genome insert in pBRpGOXA11 with the amino acid sequence of *A. niger* GO encoded in the nucleotide sequence shown in FIG. 5B is shown in FIG. 17. In the figure, the aligned sequences are suggestive that the putative Penicillium GO clone starts at amino acid 64 in the *A. niger* sequence. In addition, the proteins appear to be about 52% identical at the amino acid level.

Deposit of Biological Materials

A polynucleotide construct containing the GO-cDNA of clone 2 was deposited with the American Type Culture Collection (ATCC), 12301 Parklawn Drive, Rockville, Md., U.S.A., and will be maintained under the provisions of the Budapest Treaty. Upon allowance and issuance of the herein application as a U.S. patent, all restriction on availability of this deposit will be irrevocably removed; and access to this deposit will be available during pendency of the above-named application to one determined by the Commissioner to be entitled thereto under 37 CFR 1.14 and 35 USC 1.22. The deposit will be maintained for a period of thirty (30) years from the date of deposit, or for five (5) years after the last request for the deposit; or for the enforceable life of the U.S. patent, whichever is longer. The accession number and date of deposit are listed below.

| Deposited Material | ATCC Number | Deposit Date |
| --- | --- | --- |
| pBR-lambda-2a | 67731 | 16 June 1988 |
| pSGO3C521S | 40619 | 16 June 1989 |
| pBRpGOXA11 | 68012 | 16 June 1989 |

This deposit is provided for the convenience of those skilled in the art. It is neither an admission that such deposit is required to practice the present invention nor that equivalent embodiments are not within the skill of the art in view of the present disclosure. The public availability of this deposit is not a grant of a license to make, use or sell the deposited material under this or any other patent. The nucleic acid sequence of the deposited material is incorporated in the present disclosure closure by reference, and is controlling if in conflict with any sequences described herein.

Although the foregoing invention has been described in some detail for the purpose of illustration, it will be obvious that changes and modifications may be practiced within the scope of the appended claims by those of ordinary skill in the art.

Industrial Applicability

The provision of recombinant polynucleotides encoding GO make possible methods which are based on the expression of the polypeptide in recombinant systems. These methods and recombinant systems are particularly useful since they allow for the large scale production of the desired product. They also make possible the production of the polypeptides in systems from which they may be more easily and more economically purified, since expression vectors can be constructed which cause the product to be secreted into the medium. This would increase the availability and/or decrease the cost of GO for its many commercial purposes, for example, for the detection and estimation of glucose in industrial solutions, and in body fluids such as blood and urine.

In addition, methods which utilize recombinant systems encoding GO allow the production of GO in systems which are compatible with the intended use of the expressed product. For example, GO is used in desugaring eggs, in the removal of oxygen from beverages, moist food products, flavors, and hermetically sealed food packages. Production of the GO polypeptide in yeasts which are approved for use in food products would be advantageous, since the need for stringent purification would be less than if the polypeptide is produced in its native source, *A. niger*, which is not approved for food products, and which is highly allergenic.

Moreover, these methods and recombinant systems allow for the productions of analogs of GO, and fragments of GO, which could find commercial use in detection procedures. For example, GO fusion proteins could act in place of a labeled antibody or conjugate in a sandwich type assay. The molecule could be fused to an epitope recognized by an antibody which is to be detected. The presence of the antibody-epitope complex would be determined by detecting the enzymatic activity of glucose oxidase present. When coupled to the horseradish peroxidase assay, this would allow a colorimetric procedure to detect the presence of the antibody.

GO fusion proteins may also be beneficial in medical procedures. For example, hydrogen peroxide is toxic to a variety of bacteria and cells. It may be possible to target the enzyme to specific pathogens and/or cells by fusing GO to antibodies which would recognize these specific targets.

Inactive polypeptides which are fragments of GO or of analogs of GO may be used to raise antibodies to GO, both polyclonal and monoclonal. These antibodies are useful for the purification of GO and polypeptides substantially similar to GO by immunoaffinity procedures.

I claim:

1. A recombinant molecule comprising a polynucleotide encoding a polypeptide which exhibits glucose oxidase activity, wherein said polynucleotide encodes the polypeptide shown in FIG. 5B.

2. The molecule of claim 1, further comprising expression control sequences operationally linked to said polynucleotide, wherein the expression control sequences control expression of the polypeptide.

3. The molecule of claim 2, further comprising a secretion control sequence which controls secretion of the polypeptide.

4. The molecule of claim 2, wherein the expression control sequences control expression of the polypeptide in prokaryotic cells.

5. The molecule of claim 2, wherein the expression control sequences control expression of the polypeptide in eukaryotic cells.

6. The molecule of claim 5, wherein the expression control sequences control expression of the polypeptide in yeast.

7. The molecule of claim 6, further comprising a secretion control sequence.

8. The molecule of claim 3, wherein the expression control sequences comprise the ADH2-GAP hybrid promoter and the GAP terminator, and the secretion control sequence is selected from the group consisting of the alpha factor sequence and the GO prepro sequence.

9. The molecule of claim 8, wherein the molecule is selected from the group consisting of pAB24AGS-$_{GO}$GO, pAB24AG$_{alpha}$GO, pAB24AGSGO, and pAB24AG↕GO.

10. A recombinant molecule comprising a polynucleotide encoding a polypeptide which exhibits glucose oxidase (GO) activity, wherein said polynucleotide has the sequence shown in FIG. 5B.

11. The molecule of claim 10, further comprising expression control sequences operationally linked to said polynucleotide, wherein the expression control sequences control expression of the polypeptide.

12. The molecule of claim 11, further comprising a secretion control sequence which controls secretion of the polypeptide.

13. The molecule of claim 11, wherein the expression control sequences control expression of the polypeptide in prokaryotic cells.

14. The molecule of claim 11, wherein the expression control sequences control expression of the polypeptide in eukaryotic cells.

15. The molecule of claim 14, wherein the expression control sequences control expression of the polypeptide in yeast.

16. The molecule of claim 15, further comprising a secretion control sequence which controls secretion of the polypeptide.

17. The molecule of claim 12, wherein the expression control sequences comprise the ADH2-GAP hybrid promoter and the GAP terminator, and the secretion control sequence is selected from the group consisting of the alpha factor and the GO prepro sequence.

18. The molecule of claim 17, wherein the molecule is selected from the group consisting of pAB24AGS-$_{GO}$GO, pAB24AG$_{alpha}$GO, pAG24AGSGO, and pAB24AG@GO.

* * * * *